(12) United States Patent
Spence et al.

(10) Patent No.: US 6,540,895 B1
(45) Date of Patent: Apr. 1, 2003

(54) MICROFABRICATED CELL SORTER FOR CHEMICAL AND BIOLOGICAL MATERIALS

(75) Inventors: Charles F. Spence, Arcadia, CA (US); Anne Y. Fu, Hacienda Heights, CA (US); Stephen R. Quake, San Marino, CA (US); Frances H. Arnold, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/325,667

(22) Filed: May 21, 1999

Related U.S. Application Data

(63) Continuation-in-part of application No. 08/932,774, filed on Sep. 23, 1997, now Pat. No. 6,221,654.
(60) Provisional application No. 60/108,894, filed on Nov. 17, 1998, and provisional application No. 60/086,394, filed on May 22, 1998.

(51) Int. Cl.[7] .................. G01N 27/26; G01N 27/447; C12M 1/36; C12M 3/00
(52) U.S. Cl. .................. 204/450; 204/451; 204/600; 204/601; 435/283.1; 435/286.1; 435/286.5; 435/286.6
(58) Field of Search ................. 204/450, 451, 204/452, 453, 600, 601, 602, 603, 604, 547, 643; 435/283.1, 286.1, 286.5, 286.6, 288.4, 288.5

(56) References Cited

U.S. PATENT DOCUMENTS

| | | | |
|---|---|---|---|
| 2,656,508 A | 10/1953 | Coulter | 324/71.1 |
| 3,560,754 A | * 2/1971 | Kamentsky | 209/559 |
| 4,581,624 A | 4/1986 | O'Connor | 251/129.06 |
| 4,585,209 A | 4/1986 | Aine et al. | 251/129.02 |
| 4,675,300 A | 6/1987 | Zare et al. | 204/452 |
| 4,786,165 A | * 11/1988 | Yamamoto et al. | 356/23 |
| 4,908,112 A | 3/1990 | Pace | 210/198.2 |
| 4,963,498 A | 10/1990 | Hillman et al. | 436/69 |

(List continued on next page.)

FOREIGN PATENT DOCUMENTS

| | | |
|---|---|---|
| EP | 0 745 682 A | 12/1996 |
| GB | 2264496 | 1/1993 |

(List continued on next page.)

OTHER PUBLICATIONS

Stefan Fieldler et al, "Dielectrophoretic Sorting of Particles and Cells in a Microsystem" Analytical Chemistry, vol. 70, No. 9, pp. 1909–1915, May 1, 1998.*

(List continued on next page.)

*Primary Examiner*—Jill Warden
*Assistant Examiner*—John S. Starsiak, Jr.
(74) *Attorney, Agent, or Firm*—Darby & Darby

(57) ABSTRACT

The invention provides a microfabricated device for sorting cells based on a desired characteristic, for example, reporter-labeled cells can be sorted by the presence or level of reporter on the cells. The device includes a chip having a substrate into which is microfabricated at least one analysis unit. Each analysis unit includes a main channel, having a sample inlet channel, typically at one end, and a detection region along a portion of its length. Adjacent and downstream from the detection region, the main channel has a discrimination region or branch point leading to at least two branch channels. The analysis unit may further include additional inlet channels, detection points, branch points, and branch channels as desired. A stream containing cells is passed through the detection region, such that on average one cell occupies the detection region at a given time. The cells can be sorted into an appropriate branch channel based on the presence or amount of a detectable signal such as an optical signal, with or without stimulation, such as exposure to light in order to promote fluorescence.

3 Claims, 14 Drawing Sheets

U.S. PATENT DOCUMENTS

| | | | |
|---|---|---|---|
| 5,032,381 A | * 7/1991 | Bronstein et al. | 424/9 |
| 5,126,022 A | 6/1992 | Soane et al. | 156/468 |
| 5,140,161 A | 8/1992 | Hillman et al. | 250/341.3 |
| 5,164,598 A | 11/1992 | Hillman et al. | 250/341.3 |
| 5,271,724 A | 12/1993 | van Lintel | 417/413.2 |
| 5,304,487 A | 4/1994 | Wilding et al. | 435/24 |
| 5,376,252 A | 12/1994 | Ohman et al. | 204/603 |
| 5,417,235 A | 5/1995 | Wise et al. | 137/1 |
| 5,452,878 A | 9/1995 | Gravensen et al. | 251/129.02 |
| 5,454,472 A | 10/1995 | Benecke et al. | 209/127.1 |
| 5,486,335 A | 1/1996 | Wilding et al. | 422/55 |
| 5,498,392 A | 3/1996 | Wilding et al. | 422/68.1 |
| 5,500,071 A | 3/1996 | Kaltenbach et al. | 156/272.8 |
| 5,512,131 A | 4/1996 | Kumar et al. | 438/736 |
| 5,558,998 A | 9/1996 | Hammond et al. | 435/6 |
| 5,571,410 A | 11/1996 | Swedberg et al. | 210/198.2 |
| 5,580,523 A | 12/1996 | Bard | 422/50 |
| 5,589,136 A | 12/1996 | Northrup et al. | 422/102 |
| 5,632,876 A | 5/1997 | Zanzucchi et al. | 204/600 |
| 5,637,469 A | 6/1997 | Wilding et al. | 435/7.21 |
| 5,639,423 A | 6/1997 | Northrup et al. | 422/50 |
| 5,641,400 A | 6/1997 | Kaltenbach et al. | 210/198.2 |
| 5,646,039 A | 7/1997 | Northrup et al. | 435/287.2 |
| 5,661,222 A | 8/1997 | Hare | 525/478 |
| 5,681,484 A | 10/1997 | Zanzucchi et al. | 216/2 |
| 5,702,618 A | 12/1997 | Saaski et al. | 216/2 |
| 5,716,852 A | 2/1998 | Yager et al. | 436/172 |
| 5,726,404 A | * 3/1998 | Brody et al. | 200/81 R |
| 5,726,751 A | 3/1998 | Altendorf et al. | 356/246 |
| 5,750,015 A | 5/1998 | Soane et al. | 204/454 |
| 5,757,482 A | 5/1998 | Fuchs et al. | 356/246 |
| 5,800,690 A | 9/1998 | Chow et al. | 204/451 |
| 5,837,200 A | * 11/1998 | Diessel et al. | 422/73 |
| 5,852,495 A | 12/1998 | Parce | 356/344 |
| 5,856,174 A | 1/1999 | Lipshutz et al. | 435/286.5 |
| 5,869,004 A | 2/1999 | Parce et al. | 422/100 |
| 5,880,071 A | 3/1999 | Parce et al. | 204/453 |
| 5,885,470 A | 3/1999 | Parce et al. | 216/33 |
| 5,904,824 A | 5/1999 | Oh | 204/601 |
| 5,922,591 A | 7/1999 | Anderson et al. | 435/287.2 |
| 5,932,100 A | 8/1999 | Yager et al. | 210/634 |
| 6,221,654 B1 | * 4/2001 | Quake et al. | 435/287.3 |

FOREIGN PATENT DOCUMENTS

| | | |
|---|---|---|
| WO | WO 91/13338 | * 9/1991 |
| WO | WO91/15750 | * 10/1991 |
| WO | WO94/05414 | 3/1994 |
| WO | WO95/33846 | 12/1995 |
| WO | WO96/04547 | 2/1996 |
| WO | WO97/02357 | 1/1997 |
| WO | WO 98 00231 A | 1/1998 |
| WO | WO 98/08931 | * 3/1998 |
| WO | WO98/52691 | 1/1999 |

OTHER PUBLICATIONS

Paul C.H. Li et al, "Transport Manipulation, and Reaction of Biological Cells On–Chip Using Electrokinetic Effects" Analytical Chemistry vol. 69, No. 8, pp. 1564–1568, Apr. 15, 1999.*

Bein, Thomas, Efficient Assays for Combinatorial Methods for the Discovery of Catalysts, *Angew. Chem. Int. Ed.* 38:3, 323–26 (1999).

J. Affholter and F. Arnold, "Engineering a Revolution," *Chemistry in Britain*, Apr. 1999, p. 48.

F. H. Arnold, *Acct. Chem. Research* 31, 125–131 (1998).

Y. Xia et al., *Angewandte Chemie International Edition* 37, 550 (1998).

Hoffmüller, U. & J. Schneider–Mergener, *Angew. Chemie. Int. Ed.* 37, 3241–3243 (1998).

J. P. Nolan, L. A. Sklar, *Nature Biotechnology* 16, 633 (1998).

Jermutus, L., L. A. Ryabova & A. Pluckthun, *Curr. Opin. Biotechnol* 9, 534–548 (1998).

L. A. Sklar, *Proc. SPIE* 3256, 144 (1998).

M.U. Kopp et al., *Science*, 280: 1046 (1998).

S. Fiedler, et al. *Analytical Chemistry* 70, 1909–1915 (1998).

Tawfik, D. and Griffiths, *A Nat. Biotechnol.* 16, 656 (1998).

Hanes, J. & Pluckthun A. *Proc. Natl. Acad. Sci., USA* 94, 4937 (1997).

P. H. Li, D. J. Harrison, *Analytical Chemistry* 69, 1564 (1997).

Roberts, R. W. & Szostak, J. W. *Proc. Natl. Acad. Sci USA* 94, 12297–12302 (1997).

Stemmer, W. P. C. *Nature*, 370, 389 (1994).

Castro, A., et al., *Anal. Chem.* 85:849–852 (1993).

D.J. Harrison et al., *Science*, 261: 895 (1993).

Goodwin, P.M., et al., *Nucleic Acids Research* 21(4):803–806 (1993).

Manz et al., *Trends in Analytical Chemistry* 10: 144–149 (1991).

A. Ashkin, J. M. Dziedzic, *Science* 235, 1517 (1987).

A. Ashkin, J. M. Dziedzic, *Nature* 330, 769 (1987).

T. N. Buican, M. J. Smyth, H. A. Verissman, *Applied Optics* 26, 5311 (1987).

Krutenat, R.C., Kirk–Othmer Concise Encyclopedia of Chemical Technology, John Wiley & Sons, New York (1985), pp. 749–752.

Angell et al., *Scientific American* 248:44–55 (1983).

Thompson, L.F., "Introduction to Lithography", ACS Symposium Series 219:1–13, (1983).

M. J. Fulwyer, *Science* 156, 910 (1974).

Ballantyne, J.P., et al., *J. Vac. Sci. Technol.* 10:1094 (1973).

M. A. Van Dilla, T. T. Trujillo, P. F. Mullaney, *Science* 163, 1213 (1969).

L. A. Kamensky, M. R. Melamed, H. Derman, *Science* 150, 630 (1965).

P. J. Crosland–Taylor, *Nature (London)* 171, 37 (1953).

A. Moldavan, *Science* 80(2069), 188 (1934).

Chou, Hou–Pu et al., *Proc. Natl. Acad. Sci. USA*, 96:11–13, Jan. 1999.

R. Sweet, "Flow Sorters for Biologic Cells." In: *Flow Cytometry and Sorting*, Melamed et al., eds. John Wiley & Sons:New York, pp. 177–189 (1979).

Todd et al., "Cell Electrophoresis." In: *Flow Cytometry and Sorting*. Melamed et al., eds. John Wiley & Sons:New York, pp. 217–229 (1979).

Xia et al., *Ange. Chem. Int. Ed.*, 37:550–575 (1998).

* cited by examiner

MICROFABRICATED CELL SORTER FOR CHEMICAL AND BIOLOGICAL MATERIALS

This application claims the benefit of priority from U.S. patent application Ser. No. 08/932,774, filed Sep. 23, 1997 now U.S. Pat. No. 6,221,684 and is a continuation-in-part thereof; U.S. Provisional Application No. 60/108,894 filed Nov. 17, 1998; and U.S. Provisional Application No. 60/086,394 filed May 22, 1998, each incorporated herein by reference in their entireties.

The U.S. Government may have certain rights in this invention pursuant to Grant No. DAAH04-96-1-0141 awarded by the Army.

BACKGROUND OF THE INVENTION

This invention relates to a method and microfabricated device for sorting cells or particles by size, charge or other identifying characteristics, for example, characteristics that can be optically detected. The invention includes a fluorescence activated cell sorter (FACS), and methods for analyzing and sorting cells by measuring a signal produced by an optically-detectable (e.g., fluorescent, ultraviolet or color change) reporter associated with the cells. The methods and apparatus of the invention allow for high sensitivity, no cross-contamination, and lower cost than conventional FACS machines. In preferred embodiments, cell sorting is performed on a microfabricated chip with a detection volume of approximately 1 to 1,000,000 femtoliters (fl), preferably about 200 to 500 fl, and most preferably about 375 fl. Sorting occurs immediately after detection. In a particular embodiment, the inlet and collection wells are incorporated on the same chip.

Sorters of the invention can function as stand-alone devices or as components of integrated microanalytical chips, and can be disposable. Living cells with a distinguishing characteristic, such as *E. coli* cells expressing a fluorescent protein, can be efficiently separated from cells lacking this characteristic. Furthermore, the cells remain viable after being extracted from the sorting device. An advantage of the invention is that it can be applied to various aspects of chemical and biological studies, e.g., cell sorting, enzyme catalysis and molecular evolution (1).

The references cited herein are referred to numerically, and are appended in a Bibliography below. All of the references are incorporated herein in their entirety.

Harrison et al. (39) disclose a microfluidic device which manipulates and stops the flow of fluid through a microfabricated chip, so that a cell can be observed after it interacts with a chemical agent. The cells and the chemical agent are loaded into the device via two different inlet channels which intersect with a main flow path. The flow of the fluid is controlled by a pressure pump or by electric fields (electrophoretic or electro-osmotic) and can be stopped so that the cells can be observed, after they mix and interact with the chemical. The cells then pass through the main flow path, which terminates in a single common waste chamber. Harrison et al. do not provide a device or method for sorting cells, nor do they suggest or motivate one having ordinary skill in the art to make and use any such device. On the contrary, cells are mixed with chemicals, observed, and are discarded as waste.

Conventional flow cell sorters, such as FACS, are designed to have a flow chamber with a nozzle and use the principle of hydrodynamic focusing with sheath flow to separate or sort biological material such as cells (2–7). In addition, most sorting instruments combine the technology of ink-jet writing and the effect of gravity to achieve a high sorting rate of droplet generation and electrical charging (8–10). Despite these advances, many failures of these instruments are due to problems in the flow chamber. For example, orifice clogging, particle adsorption and contamination in the tubing may cause turbulent flow in the jet stream. These problems contribute to the great variation in illumination and detection in conventional FACS devices. Another major problem is known as sample carryover, which occurs when remnants of previous specimens left in the channel back-flush into the new sample stream during consecutive runs. A potentially more serious problem occurs when dyes remain on the tubing and the chamber, which may give false signals to the fluorescence detection or light scattering apparatus. Although such systems can be sterilized between runs, it is costly, time consuming, inefficient, and results in hours of machine down time for bleaching and sterilization procedures.

Similarly, each cell, as it passes through the orifice, may generate a different perturbation in response to droplet formation. Larger cells can possibly change the droplet size, non-spherical cells tend to align with the long axis parallel to the flow axis, and deformable cells may elongate in the direction of the flow (9, 10). This can result in some variation in the time from the analysis to the actual sorting event. Furthermore, a number of technical problems make it difficult to generate identically charged droplets, which increases deflection error. A charged droplet may cause the next droplet of the opposite polarity to have a reduced charge. On the other hand, if consecutive droplets are charged identically, then the first droplet might have a lower potential than the second droplets, and so on. Yet, charged droplets will have a defined trajectory only if they are charged identically. In addition, increasing droplet charges may cause mutual electrostatic repulsion between adjacent droplets, which also increases deflection error. Other factors, such as the very high cost for even modest conventional FACS equipment (on the order of $250,000), the high cost of maintenance, and the requirement for trained personnel to operate and maintain the equipment have been among the main considerations that hinder this technology and its widespread accessibility and use (10). Even though the field of flow cytometry has been extensively exploited in the development of cell sorting devices, significant problems persist and remain to be addressed. Thus, there is a need for improved methods and machines for cell sorting which are fast, efficient, costeffective and disposable.

SUMMARY OF THE INVENTION

The invention provides a microfabricated device for sorting cells based on a desired characteristic, for example, reporter-labeled cells can be sorted by the presence or level of reporter on the cells. The device includes a chip having a substrate into which is microfabricated at least one analysis unit. Each analysis unit includes a main channel, having a sample inlet channel, typically at one end, and a detection region along its length. Adjacent and downstream from the detection region, the main channel has a discrimination region or branch point leading to at least two branch channels. The analysis unit may further include additional inlet channels, detection points, branch points, and branch channels as desired. A stream containing the cells, e.g., in a solution or mixture, is passed through the detection region, such that on average only one cell occupies the detection region at any given time. The cells can be sorted based on their ability to emit a detectable signal such as an optical signal, with or without stimulation, such as exposure to light in order to promote fluorescence. According to the invention, the presence or level of reporter from each cell is measured within the detection region, and each cell is directed to a selected branch channel based on the level of reporter detected or measured.

In addition to sorting fluorescent and non-fluorescent cells, the invention can also provide multiparameter analysis, such as multicolor detection or a gated window detection. For example, beads of different colors, or cells labelled with one or more chromophores, can be sorted by the invention. Sorting according to a window, or threshold, means that cells or particles are selected for sorting based on the presence of a signal above a certain value or threshold, and which is typically lower than a certain upper limit. There can also be several points of analysis on the same chip for multiple time course measurements.

The invention offers several advantages over traditional sheath flow methods. Since the channels in the present device can be made with micron dimensions, the volume of the detection region is precisely controlled and there is no need for hydrodynamic focusing. The planar geometry of the device allows the use of high numerical aperture optics, thereby increasing the sensitivity of the system. Since fluid flows continuously through the system, there is no need for droplet formation, or for charged droplets, and many challenging technical issues can be avoided. In addition, there is no aerosol formation because the system is entirely self-contained, allowing much safer sorting of biohazardous material, in comparison with conventional FACS devices. The sorting device of the invention is also disposable, which obviates the need for cleaning and sterilizing the instrument, and prevents cross-contamination between samples.

Thus, a cell sorter of the invention, such as a disposable microfabricated FACS, employs a substrate that integrates at least one inlet channel and at least two outlet channels, which meet at a branch or sorting point. In a preferred embodiment, the substrate is planar, and contains a microfluidic chip made from a silicone elastomer impression of an etched silicon wafer according replica methods in soft-lithography (11). In one embodiment, the channels meet to form a "T" (T junction). A Y-shaped junction, and other shapes and geometries may also be used. A detection region is typically upstream from the branch point. Cells are diverted into one or another outlet channel based on a predetermined characteristic that is evaluated as each cell passes through the detection region. The channels are preferably sealed to contain the flow, for example by fixing a transparent coverslip, such as glass, over the chip, to cover the channels while permitting optical examination of one or more channels or regions, particularly the detection region. In a preferred embodiment the coverslip is pyrex, anodically bonded to the chip.

In one embodiment, cells are directed into one or another of a pair of outlet channels by electrodes that apply an electric field across the branch point, which effectively directs a particular cell into a predetermined outlet or branch channel.

In another embodiment, a flow of cells is maintained through the device via a pump or pressure differential. A valve structure at the branch point permits each cell to enter only one of the branch channels depending on the measurement at the detection point. In a similar embodiment, a valve structure can be provided for each branch channel, downstream of the branch point, which allows or curtails the flow through a particular channel. Alternatively, the pressure may be adjusted within or at the outlet of each branch channel, to allow or curtail flow through the channel.

An apparatus, machine or device of the invention may include a plurality of analysis units, and in such embodiments can further include a plurality of manifolds (e.g., a fitting or point with more than one lateral outlet to permit connection of or division to branch channels). The number of manifolds typically equals the number of branch channels in one analysis unit, to facilitate collection of cells from corresponding branch channels of the different analysis units.

The microfabricated device includes a transparent coverslip (e.g., glass) bonded to the substrate and covering the channels to form a "roof" and/or "floor" for the channels. A silicon chip with an anodically bonded pyrex coverslip may be used. The channels in the device are preferably between about 1 and 500 microns in width and between about 1 and 500 microns in depth, and the detection region has a volume of between about 1 fl and 100 nl.

Where desired, an external laser, a diode or integrated semiconductor laser or a high-intensity lamp (e.g., a mercury lamp) may be used to stimulate a reporter to release a measurable or detectable signal (e.g., light energy). Measurements may be taken, for example, using a microscope in connection with an intensified charge couple device (CCD) camera, photomultiplier tube, avalanche photodiode, an integrated photodiode, or the like.

In another aspect, the invention includes a method of isolating cells having a selected threshold amount of a bound or associated optically-detectable (e.g., fluorescent, ultraviolet or color change) reporter. The method includes, (a) flowing a stream of solution containing reporter-labeled cells through a channel comprising a detection region having a selected volume, where the concentration of the cells in the solution is such that they pass through the detection region one by one, (b) determining the presence or amount of reporter on each cell as it passes through the detection region, (c) diverting cells having a selected threshold of reporter into a first branch channel, and diverting cells not having the selected threshold into a second branch channel, and (d) collecting cells diverted into one or more branch channels.

The method can be applied to diverting a cell having a selected reporter threshold into the first branch channel, in such a way that the diverting action blocks the flow into the second branch channel. That is, the second channel is blocked and the stream carries the cell having the selected reporter threshold into the first branch channel. Alternatively or in addition, the method may be used to divert a cell that does not have the selected reporter threshold into the second branch channel, by blocking the flow into the first branch channel. This can be done, for example, using a valve or valves that are actuated by an electrical or mechanical switch responsive to a reporter measurement.

The method may be applied to any cell, including prokaryotic or eukaryotic, such as bacterial, plant, animal, and the like. The method is particularly useful for the sorting of mammalian (e.g., human) blood cells, such as peripheral blood mononuclear cells (PBMCs), based on the expression of various antigens, such as HLA DR, CD3, CD4, CD8, CD11a, CD11c, CD14, CD16, CD20, CD45, CD45RA, CD62L, etc. The method can also be used to sort any cell on the basis of whether it does or does not express or produce a detectable protein, either directly or in cooperation with a reporter molecule. For example, cells that produce a fluorescent protein may be sorted from those that do not. Alternatively, a fluorescent protein can be used as a reporter, for example, by co-expression with another protein (50, 51).

Alternatively, the cell may produce a detectable substance (e.g. a fluorescent compound) through its interaction with another substance added to the fluid medium. For example, cells containing a gene for a monooxygenase enzyme may catalyze a reaction on an aromatic substrate (e.g. benzene or naphthalene) with the net result that the fluorescence, or another detectable property of the substrate, will change. This change can be detected in the detection region, and cells having that change in fluorescence can be collected based on predetermined criteria. A second reagent or coupling enzyme can be used to enhance fluorescence. See, Affholter and Arnold (50) and Joo et al. (51).

DETAILED DESCRIPTION OF THE INVENTION

Definitions

Figure 1A:
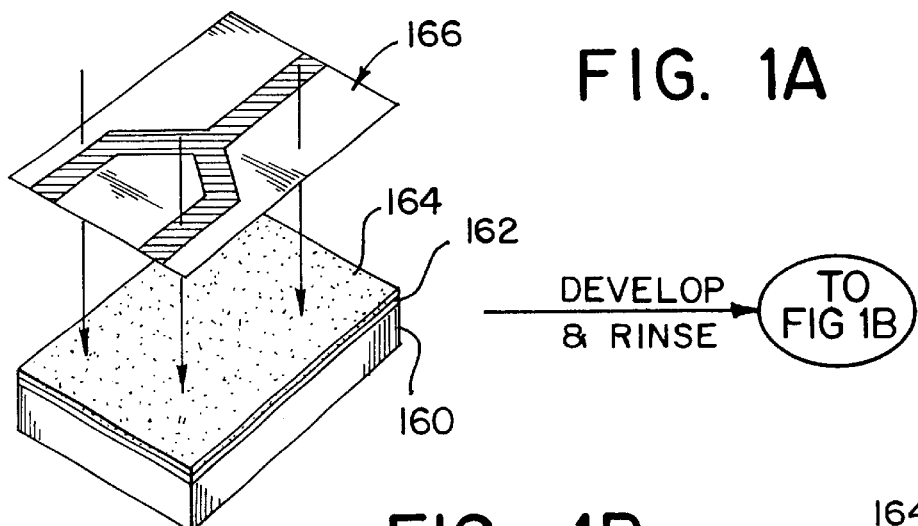
FIGS. 1A through 1D show steps in photolithographic microfabrication of a cell sorting device from a silicon wafer, using photolithography and several stages of etching.

The terms used in this specification generally have their ordinary meanings in the art, within the context of the invention, and in the specific context where each term is used. Certain terms are discussed below, or elsewhere in the specification, to provide additional guidance to the practitioner in describing the devices and methods of the invention and how to make and use them. For convenience, certain terms are highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to the preferred embodiments.

As used herein, "cell" means any cell or cells, as well as viruses or any other particles having a microscopic size, e.g. a size that is similar to that of a biological cell, and includes any prokaryotic or eukaryotic cell, e.g., bacteria, fungi, plant and animal cells. Cells are typically spherical, but can also be elongated, flattened, deformable and asymmetrical, i.e., non-spherical. The size or diameter of a cell typically ranges from about 0.1 to 120 microns, and typically is from about 1 to 50 microns. A cell may be living or dead. Since the microfabricated device of the invention is directed to sorting materials having a size similar to a biological cell (e.g. about 0.1 to 120 microns) any material having a size similar to a biological cell can be characterized and sorted using the microfabricated device of the invention. Thus, the term cell shall further include microscopic beads (such as chromatogrophic and fluorescent beads), liposomes, emulsions, or any other encapsulating biomaterials and porous materials.

Non-limiting examples include latex, glass, or paramagnetic beads; and vesicles such as emulsions and liposomes, and other porous materials such as silica beads. Beads ranging in size from 0.1 micron to 1 mm can also be used, for example in sorting a library of compounds produced by combinatorial chemistry. As used herein, a cell may be charged or uncharged. For example, charged beads may be used to facilitate flow or detection, or as a reporter. Biological cells, living or dead, may be charged for example by using a surfactant, such as SDS (sodium dodecyl sulfate).

A "reporter" is any molecule, or a portion thereof, that is detectable, or measurable, for example, by optical detection. In addition, the reporter associates with a cell or with a particular marker or characteristic of the cell, or is itself detectable, to permit identification of the cell. Such a marker includes antibodies, proteins and sugar moieties, receptors, polynucleotides, and fragments thereof. The term "label" can be used interchangeably with "reporter". The reporter is typically a dye, fluorescent, ultraviolet, or chemiluminescent agent, chromophore, or radio-label, any of which may be detected with or without some kind of stimulatory event, e.g., fluoresce with or without a reagent. In one embodiment, the reporter is a protein that is optically detectable without a device, e.g. a laser, to stimulate the reporter, such as horseradish peroxidase (HRP). A protein reporter can be expressed in the cell that is to be detected, and such expression may be indicative of the presence of the protein or it can indicate the presence of another protein that may or may not be coexpressed with the reporter. A reporter may also include any substance on or in a cell that causes a detectable reaction, for example by acting as a starting material, reactant or a catalyst for a reaction which produces a detectable product. Cells may be sorted, for example, based on the presence of the substance, or on the ability of the cell to produce the detectable product when the reporter substance is provided.

A "marker" is a characteristic of the cell that is made detectable by the reporter, or may be coexpressed with a reporter. Characteristics may include a protein, including enzyme, receptor and ligand proteins, saccharrides, polynucleotides, and combinations thereof, or any biological material associated with a cell. The product of an enzymatic reaction may also be used as a marker. The marker may be directly or indirectly associated with the reporter or can itself be a reporter.

The term "flow" means any movement of liquid or solid through a device or in a method of the invention, and encompasses without limitation any fluid stream, and any material moving with, within or against the stream, whether or not the material is carried by the stream. For example, the movement of cells through a device or in a method of the invention, e.g. through channels of a microfluidic chip of the invention, comprises a flow. This is so, according to the invention, whether or not the cells are carried by a stream of fluid also comprising a flow, or whether the cells are caused to move by some other direct or indirect force or motivation, and whether or not the nature of any motivating force is known or understood. The application of any force may be used to provide a flow, including without limitation, pressure, capillary action, electro-osmosis, electrophoresis, dielectrophoresis, optical tweezers, and combinations thereof, without regard for any particular theory or mechanism of action, so long as cells are directed for sorting according to the invention.

An "inlet region" is an area of a microfabricated chip that receives cells for sorting. The inlet region may contain an inlet channel, a well or reservoir, an opening, and other features which facilitate the entry of cells into the device. A chip may contain more than one inlet region if desired. The inlet region is in fluid communication with the main channel and is upstream therefrom.

An "outlet region" is an area of a microfabricated chip that collects or dispenses cells after sorting. An outlet region is downstream from a discrimination region, and may contain branch channels or outlet channels. A chip may contain more than one outlet region if desired.

An "analysis unit" is a microfabricated substrate, e.g., a microfabricated chip, having at least one inlet region, at least one main channel, at least one detection region and a branch point, that forms at least two branch channels and two outlet regions. A device according to the invention may comprise a plurality of analysis units.

A "main channel" is a channel of the chip of the invention which permits the flow of cells past a detection region and into a discrimination region for sorting. Both regions can be placed or fabricated into the main channel. The main channel is typically in fluid communication with an inlet channel or inlet region, which permit the flow of cells into the main channel. The main channel is also typically in fluid communication with branch channels, outlet channels, or waste channels, each of which permit the flow of cells out of the main channel.

A "detection region" is a location within the chip, typically within the main channel where cells to be sorted are examined for sorting on the basis of a predetermined characteristic. In a preferred embodiment, the cells are re-examined one at a time, and the characteristic is detected or measured optically, for example, by testing for the presence or amount of a reporter. For example, the detection region is in communication with one or more microscopes, diodes, light stimulating devices, (e.g., lasers), photomultiplier tubes, and processors (e.g., computers and software), and combinations thereof, which cooperate to detect a signal representative of a cell characteristic or reporter, and to determine and direct the sorting action at the discrimination region. The detection region is in fluid communication with a discrimination region and is at, proximate to, or upstream of the discrimination region.

A "discrimination region" or "branch point" is a junction of a channel where the flow of cells can change direction to enter one or more other channels, e.g., a branch channel, depending on a signal received in connection with an examination in the detection region. Typically, a discrimination region is monitored and/or under the control of a detection region, and therefore a discrimination region may "correspond" to such detection region. The discrimination region is in communication with and is influenced by one or more sorting techniques or flow control systems, e.g., electric, electroosmotic, (micro-) valve, etc. A flow control system can employ a variety of sorting techniques to change or direct the flow of cells into a predetermined branch channel.

A "branch channel" is a channel which is in communication with a discrimination region and a main channel. Typically, a branch channel receives cells depending on the cell characteristic of interest as detected by the detection region and sorted at the discrimination region. A branch channel may be in communication with other channels to permit additional sorting. Alternatively, a branch channel may also have an outlet region and/or terminate with a well or reservoir to allow collection or disposal of the cells.

The term "forward sorting" describes a one-direction flow of cells, typically from an inlet region (upstream) to an outlet region (downstream), and preferably without a change in direction, e.g., opposing the "forward" flow. Preferably, cells travel forward in a linear fashion, i.e., in single file. The preferred "forward" sorting algorithm consists of running the cells from the input channel to the waste channel, until a cell's fluorescence is above a preset threshold, at which point the voltages are temporarily changed to divert it to the collection channel.

The term "reversible sorting" describes a movement or flow that can change, i.e., reverse direction, for example, from a forward direction to an opposing backwards direction. Stated another way, reversible sorting permits a change in the direction of flow from a downstream to an upstream direction. This may be useful for more accurate sorting, for example, by allowing for confirmation of a sorting decision, selection of particular branch channel, or to correct an improperly selected channel.

Different algorithms for sorting in the microfluidic device can be implemented by different programs, for example under the control of a personal computer. As an example, consider a pressure-switched scheme instead of electro-osmotic flow. Electro-osmotic switching is virtually instantaneous and throughput is limited by the highest voltage that can be applied to the sorter (which also affects the run time through ion depletion effects). A pressure switched-scheme does not require high voltages and is more robust for longer runs. However, mechanical compliance in the system is likely to cause the fluid switching speed to become rate-limiting with the "forward" sorting program. Since the fluid is at low Reynolds number and is completely reversible, when trying to separate rare cells one can implement a sorting algorithm that is not limited by the intrinsic switching speed of the device. The cells flow at the highest possible static (non-switching) speed from the input to the waste. When an interesting cell is detected, the flow is stopped. By the time the flow stops, the cell may be past the junction and part way down the waste channel. The system is then run backwards at a slow (switchable) speed from waste to input, and the cell is switched to the collection channel when it passes through the detection region. At that point, the cell is saved and the device can be run at high speed in the forward direction again. This "reversible" sorting method is not possible with standard FACS machines and is particularly useful for collecting rare cells or making multiple time course measurements of a single cell.

Cell Sorter Architecture and Method

A cell sorter according to the invention comprises at least one analysis unit having an inlet region in communication with a main channel, a detection region within or coincident with a portion of the main channel, a detector associated with the detection region, a discrimination region or branch point in communication with the main channel and with branch channels, and a flow control responsive to the detector. The branch channels may each lead to an outlet region and to a well or reservoir. The inlet region may also communicate with a well or reservoir. As each cell passes into the detection region, it is examined for a predetermined characteristic (i.e. using the detector), and a corresponding signal is produced, for example indicating that "yes" the characteristic is present, or "no" it is not. In response to this signal, a flow control can be activated to divert a cell or cells into one branch channel or another. Thus, a cell or cells within the discrimination region can be sorted into an appropriate branch channel according to a signal produced by the corresponding examination at the detection region. Optical detection of cell characteristics is preferred, for example directly or by use of a reporter associated with a characteristic chosen for sorting. However, other detection techniques may also be employed.

A variety of channels for sample flow and mixing can be microfabricated on a single chip and can be positioned at any location on the chip as the detection and discrimination or sorting points, e.g., for kinetic studies (12, 14). A plurality of analysis units of the invention may be combined in one device. Microfabrication applied according to the invention eliminates the dead time occurring in conventional flow cytometric kinetic studies, and achieves a better time-resolution. Furthermore, linear arrays of channels on a single chip, i.e., a multiplex system, can simultaneously detect and sort a sample by using an array of photomultiplier tubes (PMT) for parallel analysis of different channels (15). This arrangement can be used to improve throughput or for successive sample enrichment, and can be adapted to provide a very high throughput to the microfluidic devices that exceeds the capacity permitted by conventional flow sorters. Moreover, microfabrication permits other technologies to be integrated or combined with flow cytometry on a single chip, such as PCR (21), moving cells using optical tweezer/cell trapping (16–18), transformation of cells by electroporation (19), $\mu$TAS (22), and DNA hybridization (6). Detectors and/or light filters that are used to detect cell characteristics or the reporters can also be fabricated directly on the chip.

A device of the invention can be microfabricated with a sample solution reservoir or well at the inlet region, which is typically in fluid communication with an inlet channel. A reservoir may facilitate introduction of cells into the device and into the sample inlet channel of each analysis unit. An inlet region may have an opening, such as in the floor of the microfabricated chip, to permit entry of the cell sample into the device. The inlet region may also contain a connector adapted to receive a suitable piece of tubing, such as liquid chromatography or HPLC tubing, through which a sample may be supplied. Such an arrangement facilitates introducing the sample solution under positive pressure in order to achieve a desired flow rate through the channels. Outlet channels and wells can be similarly provided.

Substrate and Flow Channels

A typical analysis unit of the invention comprises an inlet region that is part of and feeds or communicates with a main channel, which in turn communicates with two (or more) branch channels at a junction or branch point, forming for example a T-shape or a Y-shape. Other shapes and channel geometries may be used as desired. The region at or surrounding the junction can also be referred to as a discrimination region, however, precise boundaries for the discrimination region are not required. A detection region is identified within or coincident with a portion of the main channel downstream of the inlet region, and at or upstream of the discrimination region or branch point. Precise boundaries for the detection region are not required, but are preferred. The discrimination region may be located immediately downstream of the detection region, or it may be separated by a suitable distance. Preferably, the distance between the detection and discrimination regions is from about 0.1 to about 100 microns, to facilitate rapid discrimination and sorting of single cells at high switching speeds, in response to the examination of cells in the detection region. It will be appreciated that the channels can have any suitable shape or cross-section, such as tubular or grooved, and can be arranged in any suitable manner, so long as a flow of cells can be directed from one channel into at least one of two or more branch channels.

The channels of the invention are microfabricated, for example by etching a silicon chip using conventional photolithography techniques, or using a micromachining technology called "soft lithography", developed in the late 1990's (11). These and other microfabrication methods may be used to provide inexpensive miniaturized devices, and in the case of soft lithography, can provide robust devices having beneficial properties such as improved flexibility, stability, and mechanical strength. When optical detection is employed, the invention also provides minimal light scatter from cell suspension and chamber material. Devices according to the invention are relatively inexpensive and easy to set up. They can also be disposable, which greatly relieves many of the concerns of sterilization and permanent adsorption of particles unto the flow chambers and channels of conventional FACS machines. Using these kinds of techniques, microfabricated fluidic devices can replace the conventional fluidic flow chambers of the prior art.

A microfabricated cell sorting device of the invention is preferably fabricated from a silicon microchip or silicon elastomer. The dimensions of the chip are those of typical microchips, ranging between about 0.5 cm to about 5 cm per side and about 1 micron to about 1 cm in thickness. The device contains at least one analysis unit containing a main channel having detection and discrimination regions. Preferably a device also contains at least one inlet region (which may contain an inlet channel) and two or more outlet regions (which have fluid communication with a branch channel in each region). It shall be appreciated that the "regions" and "channels" are in fluid communication with each other, and therefore they may overlap, i.e., there may be no clear boundary where a region or channel begins or ends. A microfabricated device can be covered with a material having transparent properties, e.g., a glass coverslip to permit detection of a reporter for example by an optical device, such as an optical microscope.

The dimensions of the channels and in particular of the detection region are influenced by the size of the cells under study. These cells can be rather large by molecular standards. For example, mammalian cells can have a diameter of about 1 to 50 microns, more typically 10 to 30 microns, although fat cells can be larger than 120 microns, and plant cells are generally 10 to 100 microns. Accordingly, detection regions used for detecting cells in this size range have a cross-sectional area large enough to allow a desired cell to pass through without being substantially slowed down relative to the flow of the solution carrying it. To avoid "bottlenecks" and/or turbulence, and promote single-file flow, the channel dimensions, particularly in the detection region, should generally be at least about twice, preferably at least about five times as large per side or in diameter as the diameter of the largest cell that will be passing through it.

A microfabricated device of the invention is adapted for handling particles on the size scale of cells, and is dependent on the dimensions of the microfabricated channels, detection and discrimination regions. Specifically, the channels in a device are typically between about 2 and 500 microns in width and between about 2 and 500 microns in depth, to allow for an orderly flow of cells in the channels. Similarly, the volume of the detection region in a cell sorting device is typically in the range of between about 1 femtoliter (fl) and 1 nanoliter (nl).

To prevent the cells from adhering to the sides of the channels, the channels (and coverslip, if used) may have a coating which minimizes cell adhesion. Such a coating may be intrinsic to the material from which the device is manufactured, or it may be applied after the structural aspects of the channels have been microfabricated. "TEFLON" is an example of a coating that has suitable surface properties.

A silicon substrate containing the microfabricated flow channels and other components is preferably covered and sealed, most preferably with a transparent cover, e.g., thin glass or quartz, although other clear or opaque cover materials may be used. When external radiation sources or detectors are employed, the detection region is covered with a clear cover material to allow optical access to the cells. For example, anodic bonding to a "PYREX" cover slip can be accomplished by washing both components in an aqueous $H_2SO_4/H_2O_2$ bath, rinsing in water, and then, for example, heating to about 350 degrees C while applying a voltage of 450V.

Switching and Flow Control

Electro-osmotic and pressure-driven flow are examples of methods or systems for flow control, that is, manipulating the flow of cells, particles or reagents in one or more directions and/or into one or more channels of a microfluidic device of the invention (8, 12, 13, 23). Other methods may also be used, for example, electrophoresis and dielectrophoresis. In certain embodiments of the invention, the flow moves in one "forward" direction, e.g. from the inlet region through the main and branch channels to an outlet region. In other embodiments the direction of flow is reversible. Application of these techniques according to the invention provides more rapid and accurate devices and methods for sorting cells, for example, because the sorting occurs at or in a discrimination region that can be placed at or immediately after a detection region. This provides a shorter distance for cells to travel, cells can move more rapidly and with less turbulence, and can more readily be moved, examined, and sorted in single file, i.e., one cell at a time. In a reversible embodiment, potential sorting errors can be avoided, for example by reversing and slowing the flow to re-read or resort a cell or cells before irretrievably committing the cell or cells to a particular branch channel.

Without being bound by any theory, electro-osmosis is believed to produce motion in a stream containing ions, e.g. a liquid such as a buffer, by application of a voltage differential or charge gradient between two or more electrodes. Neutral (uncharged) cells can be carried by the stream. Electro-osmosis is particularly suitable for rapidly changing the course, direction or speed of flow. Electrophoresis is believed to produce movement of charged objects in a fluid toward one or more electrodes of opposite charge, and away from one on or more electrodes of like charge.

Dielectrophoresis is believed to produce movement of dielectric objects, which have no net charge, but have regions that are positively or negatively charged in relation to each other. Alternating, non-homogeneous electric fields in the presence of particles, such as cells or beads, cause them to become electrically polarized and thus to experience dielectrophoretic forces. Depending on the dielectric polarizability of the particles and the suspending medium, dielectric particles will move either toward the regions of high field strength or low field strength. For example, the polarizability of living cells depends on their composition, morphology, and phenotype and is highly dependent on the frequency of the applied electrical field. Thus, cells of different types and in different physiological states generally possess distinctly different dielectric properties, which may provide a basis for cell separation, e.g., by differential dielectrophoretic forces. According to formulas provided in Fiedler et al. (13), individual manipulation of single particles requires field differences (inhomogeneties) with dimensions close to the particles. Manipulation is also dependent on permittivity (a dielectric property) of the particles with the suspending medium. Thus, polymer particles and living cells show negative dielectrophoresis at high-field frequencies in water. For example, dielectrophoretic forces experienced by a latex sphere,in a 0.5 MV/m field (10V for a 20 micron electrode gap) in water are predicted to be about 0.2 piconewtons (pN) for a 3.4 micron latex sphere to 15 pN for a 15 micron latex sphere (13). These values are mostly greater than the hydrodynamic forces experienced by the sphere in a stream (about 0.3 pN for a 3.4 micron sphere and 1.5 pN for a 15 micron sphere). Therefore, manipulation of individual cells or particles can be accomplished in a streaming fluid, such as in a cell sorter device, using dielectrophoresis. Using conventional semiconductor technologies, electrodes can be microfabricated onto a substrate to control the force fields in a microfabricated sorting device of the invention.

Dielectrophoresis is particluarly suitable for moving objects that are electrical conductors. The use of AC current is preferred, to prevent permanent alignment of ions. Megahertz frequencies are suitable to provide a net alignment, attractive force, and motion over relatively long distances. See e.g. Benecke (49).

Optical tweezers can also be used in the invention to trap and move objects, e.g cells, with focused beams of light such as lasers. Flow can also be obtained and controlled by providing a pressure differential or gradient between one or more channels of a device or in a method of the invention.

Detection and Discrimination for Sorting

The detector can be any device or method for interrogating a cell as it passes through the detection region. Typically, cells are to be sorted according to a predetermined characteristic that is directly or indirectly detectable, and the detector is selected or adapted to detect that characteristic. A preferred detector is an optical detector, such as a microscope, which may be coupled with a computer and/or other image processing or enhancement devices to process images or information produced by the microscope using known techniques. For example, cells can be sorted for whether they contain or produce a particular protein, by using an optical detector to examine each cell for an optical indication of the presence or amount of that protein. The protein may itself be detectable, for example by a characteristic fluorescence, or it may be labeled or associated with a reporter that produces a detectable signal when the desired protein is present, or is present in at least a threshold amount. There is no limit to the kind or number of cell characteristics that can be identified or measured using the techniques of the invention, which include without limitation surface characteristics of the cell and intracellular characteristics, provided only that the characteristic or characteristics of interest for sorting can be sufficiently identified and detected or measured to distinguish cells having the desired characteristic(s) from those which do not. For example, any label or reporter as described herein can be used as the basis for sorting cells, i.e. detecting cells to be collected.

In a preferred embodiment, the cells are separated based on the intensity of a signal from an optically-detectable reporter bound to or associated with the cells as they pass through a detection window or "detection region" in the device. Cells having an amount or level of the reporter at a selected threshold or within a selected range are diverted into a predetermined outlet or branch channel of the device. The reporter signal is collected by a microscope and measured by a photomultiplier tube (PMT). A computer digitizes the PMT signal and controls the flow via valve action or electroosmotic potentials.

In one embodiment, the chip is mounted on an inverted optical microscope. Fluorescence produced by a reporter is excited using a laser beam focused on cells passing through a detection region. Fluorescent reporters include, e.g., rhodamine, fluorescein, Texas red, Cy 3, Cy 5, and phycobiliprotein. Thus, in one aspect of the invention, the sorting device can sort cells based on the level of expression of selected cell markers, such as cell surface markers, which have a detectable reporter bound thereto, in a manner similar to that currently employed using fluorescence-activated cell sorting (FACS) machines. Proteins or other characteristics within a cell, and which do not necessarily appear on the cell surface, can also be identified and used as a basis for sorting. The sorted cells can be collected from the outlet channels and used as needed.

To determine whether a cell has a desired characteristic, the detection region may include an apparatus for stimulating a reporter for that characteristic to emit measurable light energy, e.g., a light source such as a laser, laser diode, high-intensity lamp, (e.g., mercury lamp), and the like. In embodiments where a lamp is used, the channels are preferably shielded from light in all regions except the detection region. In embodiments where a laser is used, the laser can be set to scan across a set of detection regions from different analysis units. In addition, laser diodes may be microfabricated into the same chip that contains the analysis units. Alternatively, laser diodes may be incorporated into a second chip (i.e., a laser diode chip) that is placed adjacent to the microfabricated sorter chip such that the laser light from the diodes shines on the detection region(s).

In preferred embodiments, an integrated semiconductor laser and/or an integrated photodiode detector are included on the silicon wafer in the vicinity of the detection region. This design provides the advantages of compactness and a shorter optical path for exciting and/or emitted radiation, thus minimizing distortion.

Sorting Schemes

According to the invention, cells are sorted dynamically in a flow stream of microscopic dimensions, based on the detection or measurement of a characteristic, marker or reporter that is associated with the cells. The stream is typically but not necessarily continuous, and may be stopped and started, reversed, or changed in speed. Prior to sorting, a liquid that does not contain cells can be introduced at an inlet region of the chip (e.g., from an inlet well or channel) and is directed through the device by capillary action, to hydrate and prepare the device for sorting. If desired, the pressure can be adjusted or equalized for example by adding buffer to an outlet region. The liquid typically is an aqueous buffer solution, such as ultrapure water (e.g., 18 mega ohm resistivity, obtained for example by column chromatography), ultrapure water, 10 mM Tris HCL and 1 mM EDTA (TE), phosphate buffer saline (PBS), and acetate buffer. Any liquid or buffer that is physiologically compatible with the population of cells to be sorted can be used.

A sample solution containing a mixture or population of cells in a suitable carrier fluid (such as a liquid or buffer described above) is supplied to the inlet region. The capillary force causes the sample to enter the device. The force and direction of flow can be controlled by any desired method for controlling flow, for example, by a pressure differential, by valve action, or by electro-osmotic flow, e.g., produced by electrodes at inlet and outlet channels. This permits the movement of the cells into one or more desired branch channels or outlet regions.

A "forward" sorting algorithm, according to the invention, includes embodiments where cells from an inlet channel flow through the device to a predetermined branch or outlet channel (which can be called a "waste channel"), until the level of measurable reporter of a cell is above a pre-set threshold. At that time, the flow is diverted to deliver the cell to another channel. For example, in an electro-osmotic embodiment, where switching is virtually instantaneous and throughput is limited by the highest voltage, the voltages are temporarily changed to divert the chosen cell to another predetermined outlet channel (which can be called a "collection channel"). Sorting, including synchronizing detection of a reporter and diversion of the flow, can be controlled by various methods including computer or microprocessor control. Different algorithms for sorting in the microfluidic device can be implemented by different computer programs, such as programs used in conventional FACS devices. For example, a programmable card can be used to control switching, such as a Lab PC 1200 Card, available from National Instruments, Austin, Tex. Algorithms as sorting procedures can be programmed using C++, LABVIEW, or any suitable software.

A "reversible" sorting algorithm can be used in place of a "forward" mode, for example in embodiments where switching speed may be limited. For example, a pressure-switched scheme can be used instead of electro-osmotic flow and does not require high voltages and may be more robust for longer runs. However, mechanical constraints may cause the fluid switching speed to become rate-limiting. In a pressure-switched scheme the flow is stopped when a cell of interest is detected. By the time the flow stops, the cell may be past the junction or branch point and be part of the way down the waste channel. In this situation, a reversible embodiment can be used. The system can be run backwards at a slower (switchable) speed (e.g., from waste to inlet), and the cell is then switched to a different branch or collection channel. At that point, a potentially mis-sorted cell is "saved", and the device can again be run at high speed in the forward direction. This "reversible" sorting method is not possible with standard FACS machines. FACS machines mostly sort aerosol droplets which cannot be reversed back to the chamber, in order to be redirected. The aerosol droplet sorter are virtually irreversible. Reversible sorting is particularly useful for identifying rare cells (e.g., in molecular evolution and cancer cytological identification), or cells few in number, which may be misdirected due to a margin of error inherent to any fluidic device. The reversible nature of the device of the invention permits a reduction in this possible error.

In addition, a "reversible" sorting method permits multiple time course measurements of a single cell. This allows for observations or measurements of the same cell at different times, because the flow reverses the cell back into the detection window again before redirecting the cell into a different channel. Thus, measurements can be compared or confirmed, and changes in cell properties over time can be examined, for example in kinetic studies.

When trying to separate cells in a sample at a very low ratio to the total number of cells, a sorting algorithm can be implemented that is not limited by the intrinsic switching speed of the device. Consequently, the cells flow at the highest possible static (non-switching) speed from the inlet channel to the waste channel. Unwanted cells can be directed into the waste channel at the highest speed possible, and when a desired cell is detected, the flow can be slowed down and then reversed, to direct the cell back into the detection region, from where it can be redirected (i.e. to accomplish efficient switching). Hence the cells can flow at the highest possible static speed.

Preferably, the fluid carrying the cells has a relatively low Reynolds Number, for example $10^{-2}$. The Reynolds Number represents an inverse relationship between the density and velocity of a fluid and its viscosity in a channel of given length. More viscous, less dense, slower moving fluids over a shorter distance will have a lower Reynolds Number, and are easier to divert, stop, start, or reverse without turbulence. Because of the small sizes and slow velocities, microfabricated fluid systems are often in a low Reynolds number regime (Re<<1). In this regime, inertial effects, which cause turbulence and secondary flows, are negligible; viscous effects dominate the dynamics. These conditions are advantageous for sorting, and are provided by microfabricated devices of the invention. Accordingly the microfabricated devices of the invention are preferably if not exclusively operated at a low or very low Reynold's number.

Figure 14A:
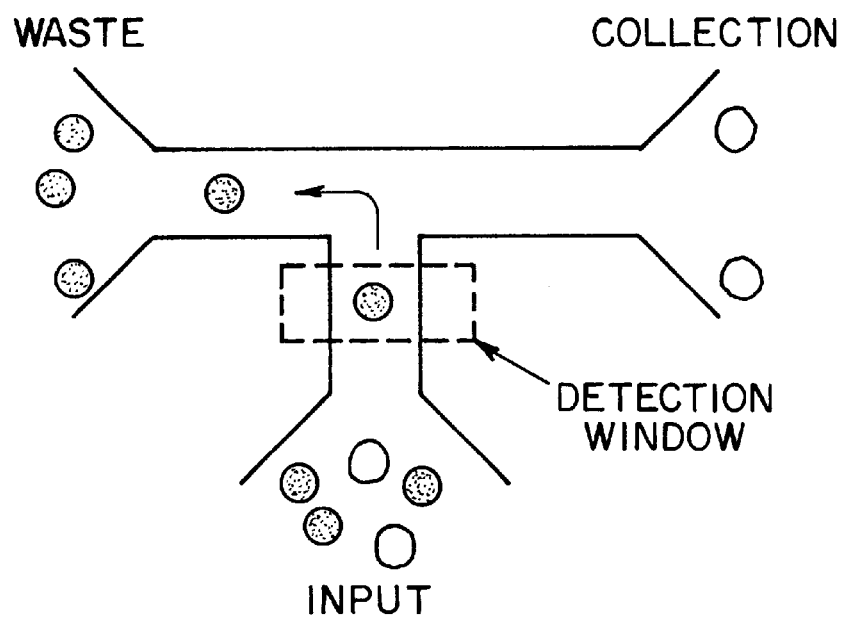
FIGS. 14A and B show a sorting scheme according to the invention, in diagrammatic form.
Figure 14B:
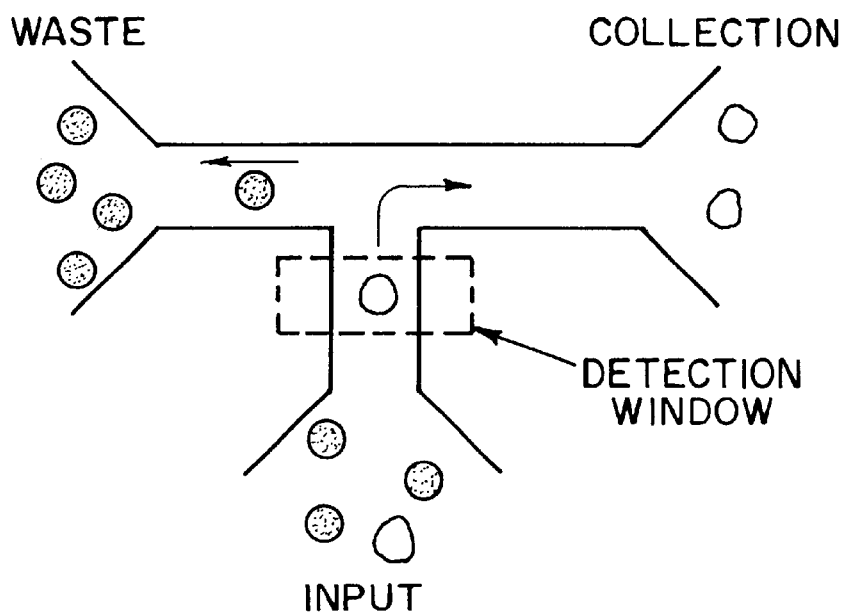
Figure 15A:
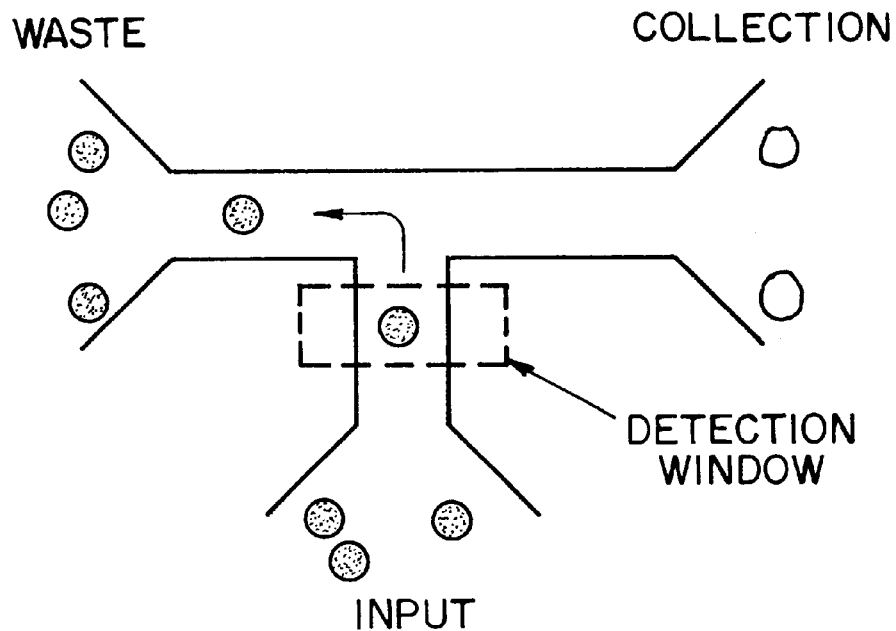
FIGS. 15A and B show a reversible sorting scheme according to the invention.
Figure 15B:
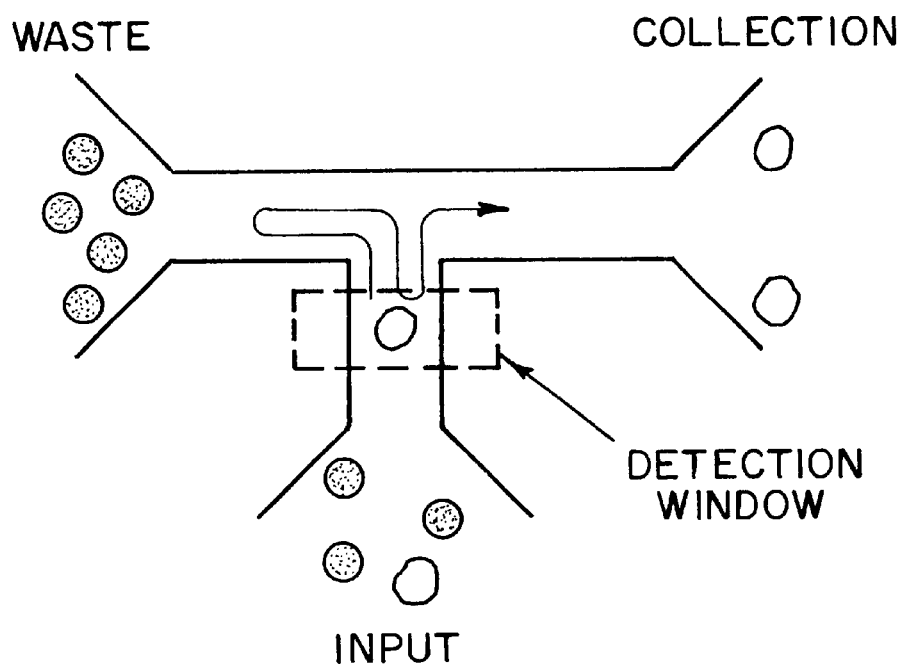

Exemplary sorting schemes are shown diagrammatically in FIGS. 14A and B and FIGS. 15A and B.

EXAMPLES

Example 1

Microfabrication of a Silicon Device

Analytical devices having microscale flow channels, valves and other elements can be designed and fabricated from a solid substrate material. Silicon is a preferred substrate material due to well-developed technology permitting its precise and efficient fabrication, but other materials may be used, including polymers such as polytetrafluoroethylenes. Micromachining methods well known in the art include film deposition processes, such as spin coating and chemical vapor deposition, laser fabrication or photolithographic techniques, or etching methods, which may be performed by either wet chemical or plasma processes. See, e.g., (37) and (38).

FIGS. 1A–1D illustrate the initial steps in microfabricating the channels and discrimination region of a cell sorting device of the invention by photolithographic techniques. As shown, the structure includes a silicon substrate 160. The silicon wafer which forms the substrate is typically washed in a 4:1 $H_2SO_4/H_2O_2$ bath, rinsed in water, and spun dry. A layer 162 of silicon dioxide, preferably about 0.5 µm in thickness, is formed on the silicon, typically by heating the silicon wafer to 800 to 1200 degrees C. in an atmosphere of steam. The oxide layer is then coated with a photoresist layer 164, preferably about 1 µm in thickness. Suitable negative- or positive-resist materials are well known. Common negative-resist materials include two-component bisarylazide/rubber resists. Common positive-resist materials include polymethyl-methacrylate (PMMA) and two component diazoquinone/phenolic resin materials. See, e.g., (36).

The coated laminate is irradiated through a photomask 166 which has been imprinted with a pattern corresponding in size and layout to the desired pattern of the microchannels. Methods for forming photomasks having desired photomask patterns are well known. For example, the mask can be prepared by printing the desired layout on an overhead transparency using a high resolution (3000 dpi) printer. Exposure is carried out on standard equipment such as a Karl Suss contact lithography machine.

In the method illustrated in FIGS. 3A–3D, the photoresist is a negative resist. Thus, exposure of the resist to a selected wavelength, e.g., UV light, produces a chemical change that renders the exposed resist material resistant to the subsequent etching step. Treatment with a suitable etchant removes the unexposed areas of the resist, leaving a pattern of bare and resist-coated silicon oxide on the wafer surface, corresponding to the layout and dimensions of the desired microstructures. In this embodiment, since a negative resist is used, the bare areas correspond to the printed layout on the photomask. The wafer is next treated with a second etchant material, such as a reactive ion etch (RIE), which effectively dissolves the exposed areas of silicon dioxide. The remaining resist is removed, typically with hot aqueous $H_2SO_4$. The remaining pattern of silicon dioxide (162) now serves as a mask for the silicon (160). The channels are etched in the unmasked areas of the silicon substrate by treating with a KOH etching solution. Depth of etching is controlled by time of treatment. Additional microcomponents may also be formed within the channels by further photolithography and etching steps, as discussed below.

Depending on the method to be used for directing the flow of cells through the device, e.g., electro-osmotic or microvalve, electrodes and/or valves are fabricated into the flow channels. A number of different techniques are available for applying thin metal coatings to a substrate in a desired pattern. These are reviewed, for example, in (32). A convenient and common technique used in fabrication of microelectronic circuitry is vacuum deposition. For example, metal electrodes or contacts may be evaporated onto a substrate using vacuum deposition and a contact mask made from, for example, a "MYLAR" sheet. Various metals such as platinum, gold, silver or indium/tin oxide may be used for the electrodes.

Deposition techniques allowing precise control of the area of deposition are preferred when applying electrodes to the side walls of the channels in the device of the invention. Such techniques are described, for example, in (32) and the references cited therein. These techniques include plasma spraying, where a plasma gun accelerates molten metal particles in a carrier gas towards the substrate, and physical vapor deposition using an electron beam to deliver atoms on line-of-sight to the substrate from a virtual point source. In laser coating, a laser is focused onto the target point on the substrate, and a carrier gas projects powdered coating material into the beam, so that the molten particles are accelerated toward the substrate. Another technique allowing precise targeting uses an electron beam to induce selective decomposition of a previously deposited substance, such as a metal salt, to a metal. This technique has been used to produce submicron circuit paths, e.g., (26).

Example 2

Photodiode Detectors

Figure 2A:
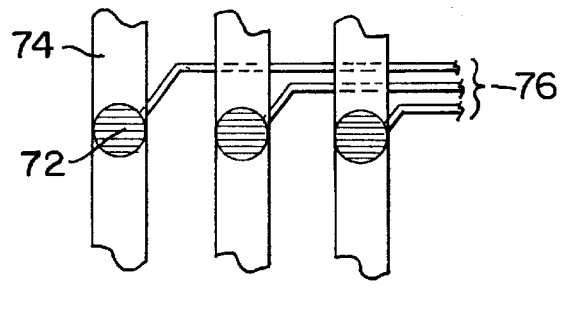
FIG. 2A shows one embodiment of a detection region used in a cell sorting device, having an integrated photodiode detector.

In one embodiment of the invention, shown in FIG. 2A, each detection region is formed from a portion of a channel 74 of an analysis unit and includes a photodiode 72 preferably located in the floor of the main channel. The detection region encompasses a receptive field of the photodiode in the channel, which receptive field has a circular shape. The volume of the detection region is the volume of a cylinder with a diameter equal to the receptive field of the photodiode and a height equal to the depth of the channel above the photodiode.

The signals from the photodiodes 72 can be carried to a processor via one or more lines 76, representing any form of electrical communication (including e.g. wires, conductive lines etched in the substrate, etc.). The processor acts on the signals, for example by processing them into values for comparison with a predetermined set of values for sorting the cells. In one embodiment, the values correspond to the amount of optically detectable signal emitted from a cell, which is indicative of a particular cell type or characteristic giving rise to the signal. The processor uses this information (i.e., the values) to control active elements in the discrimination region to determine how to sort the cells (e.g. electro-osmotic switching or valve action).

When more than one detection region is used, the photodiodes in the laser diode chip are preferably spaced apart relative to the spacing of the detection regions in the analysis unit. That is, for more accurate detection, the photodiodes are placed apart at the same spacing as the spacing of the detection region.

The processor can be integrated into the same chip that contains the analysis unit(s), or it can be separate, e.g., an independent microchip connected to the analysis unit-containing chip via electronic leads that connect to the detection region(s) and/or to the discrimination region(s), such as by a photodiode. The processor can be a computer or microprocessor, and is typically connected to a data storage unit, such as computer memory, hard disk, or the like, and/or a data output unit, such as a display monitor, printer and/or plotter.

The types and numbers of cells, based on detection of a reporter associated with or bound to the cells passing through the detection region, can be calculated or determined, and the data obtained can be stored in the data storage unit. This information can then be further processed or routed to the data outlet unit for presentation, e.g. histograms, of the types of cells or levels of a protein, saccharide, or some other characteristic on the cell surface in the sample. The data can also be presented in real time as the sample is flowing through the device.

Figure 1B:
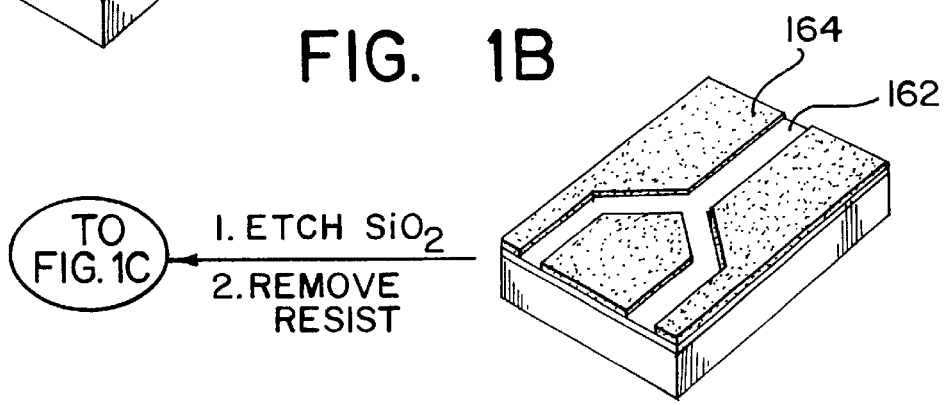
Figure 1C:
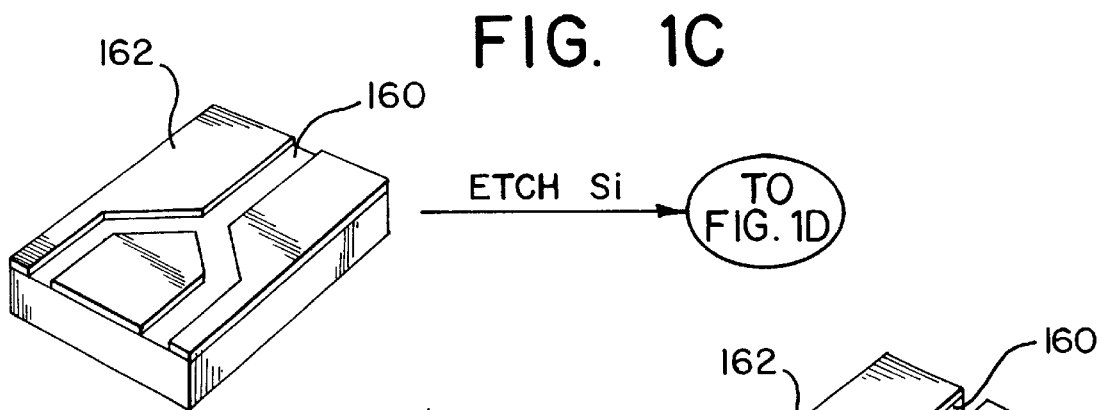
Figure 1D:
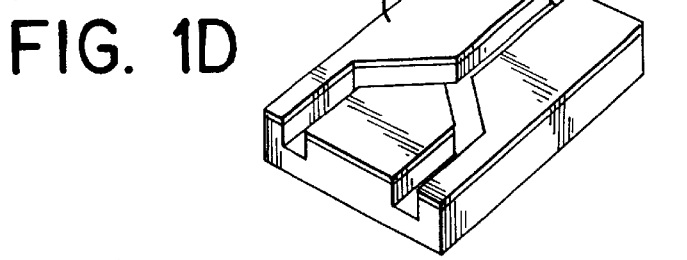

In the embodiment of FIG. 1B, the photodiode 78 is larger in diameter than the width of the channel 82, forming a detection region 80 that is longer (along the length of channel 82) than it is wide. The volume of such a detection region is approximately equal to the cross-sectional area of the channel above the diode multiplied by the diameter of the diode.

If desired, the device may contain a plurality of analysis units, i.e., more than one detection and discrimination region, and a plurality of branch channels which are in fluid communication with and branch out from the discrimination regions. It will be appreciated that the position and fate of the cells in the discrimination region can be monitored by additional detection regions installed, for example, immediately upstream of the discrimination region and/or within the branch channels immediately downstream of the branch point. The information obtained by the additional detection regions can be used by a processor to continuously revise estimates of the velocity of the cells in the channels and to confirm that cells having a selected characteristic enter the desired branch channel.

A group of manifolds (a region consisting of several channels which lead to or from a common channel) can be included to facilitate movement of the cell sample from the different analysis units, through the plurality of branch channels and to the appropriate solution outlet. Manifolds are preferably microfabricated into the chip at different levels of depth. Thus, devices of the invention having a plurality of analysis units can collect the solution from associated branch channels of each unit into a manifold, which routes the flow of solution to an outlet. The outlet can be adapted for receiving, for example, a segment of tubing or a sample tube, such as a standard 1.5 ml centrifuge tube. Collection can also be done using micropipettes.

Example 3

Valve Structures

Figure 3A:
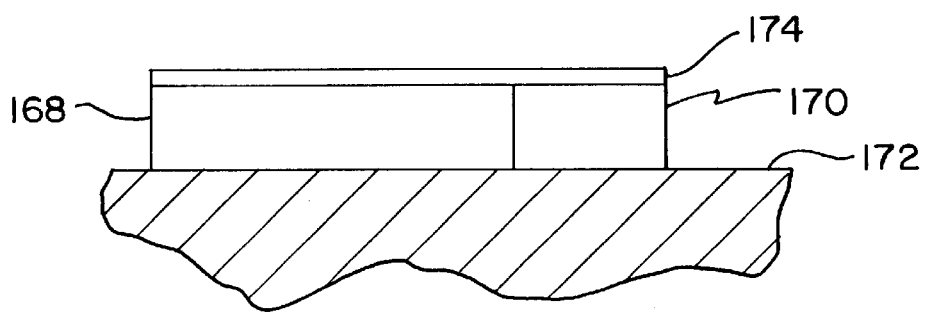
FIGS. 3A and 3B show one embodiment of a valve within a branch channel of a cell sorting device, and steps in fabrication of the valve.
Figure 3B:
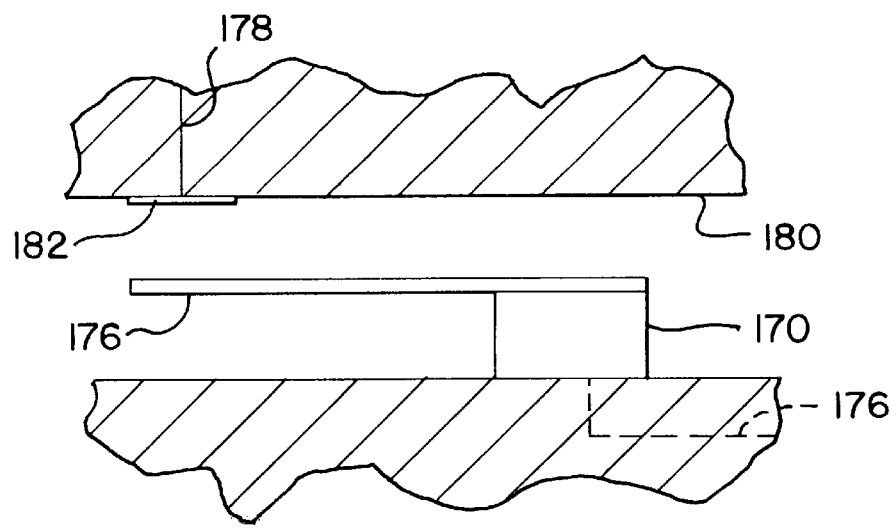

In an embodiment where pressure separation is used for discrimination of cells, valves can be used to block or unblock the pressurized flow of cells through selected channels. A thin cantilever, for example, may be included within a branch point, as shown in FIGS. 3A and 3B, such that it may be displaced towards one or the other wall of the main channel, typically by electrostatic attraction, thus closing off a selected branch channel. Electrodes are on the walls of the channel adjacent to the end of the cantilever. Suitable electrical contacts for applying a potential to the cantilever are also provided in a similar manner as the electrodes.

A valve within a channel may be microfabricated, if desired, in the form of an electrostatically operated cantilever or diaphragm. Techniques for forming such elements are well known in the art (e.g., 24, 29, 35, 36, 37). Typical processes include the use of selectively etched sacrificial layers in a multilayer structure or, for example, the undercutting of a layer of silicon dioxide via anisotropic etching. For example, to form a cantilever within a channel, as illustrated in FIGS. 3A and 3B, a sacrificial layer 168 may be formed adjacent to a small section of a non-etchable material 170, using known photolithography methods, on the floor of a channel, as shown in FIG. 3A. Both layers can then be coated with, for example, silicon dioxide or another non-etchable layer, as shown at 172. Etching of the sacrificial layer deposits the cantilever member 174 within the channel, as shown in FIG. 3B. Suitable materials for the sacrificial layer, non-etchable layers and etchant include undoped silicon, p-doped silicon and silicon dioxide, and the etchant EDP (ethylene diamine/pyrocatechol), respectively. Because the cantilever in FIG. 3B is parallel to the direction of etching, it may be formed of a thin layer of silicon by incorporating the element into the original photoresist pattern. The cantilever is preferably coated with a dielectric material such as silicon nitride, as described in (35) for example, to prevent short circuiting between the conductive surfaces.

It will be apparent to one of skill in the field that other types of valves or switches can be designed and fabricated, using well known photolithographic or other microfabrication techniques, for controlling flow within the channels of the device. Multiple layers of channels can also be prepared.

Example 4

Sorting Techniques

As illustrated with respect to FIGS. 4A–4D, there are a number of ways in which cells can be routed or sorted into a selected branch channel.

Figure 4A:
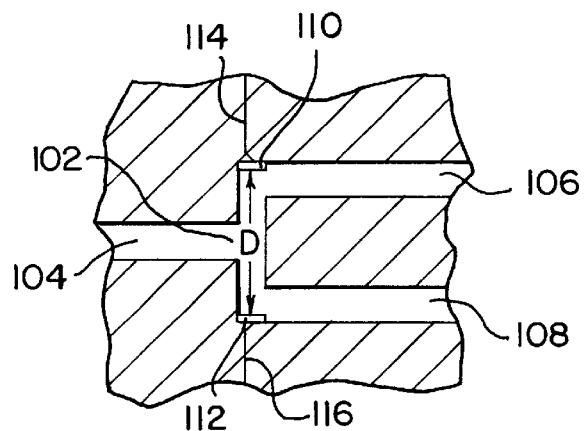
FIG. 4A shows one embodiment of a discrimination region and associated channels used in a cell sorting device, having electrodes disposed within the channels for electrophoretic discrimination.

FIG. 4A shows a discrimination region 102, which is suitable for electrophoretic discrimination as the sorting technique. The discrimination region is preceded by a main channel 104. A junction divides the main channel into two branch channels 106 and 108. The discrimination region 102 includes electrodes 110 and 112, positioned on outer side walls of the branch channels 106 and 108, and which connect to leads 114 and 116. The leads are connected to a voltage source (not shown) incorporated into or controlled by a processor (not shown), as described, infra. The distance (D) between the electrodes is preferably less than the average distance separating the cells during flow through the main channel. The dimensions of the electrodes are typically the same as the dimensions of the channels in which they are positioned, such that the electrodes are as high and wide as the channel.

Figure 4B:
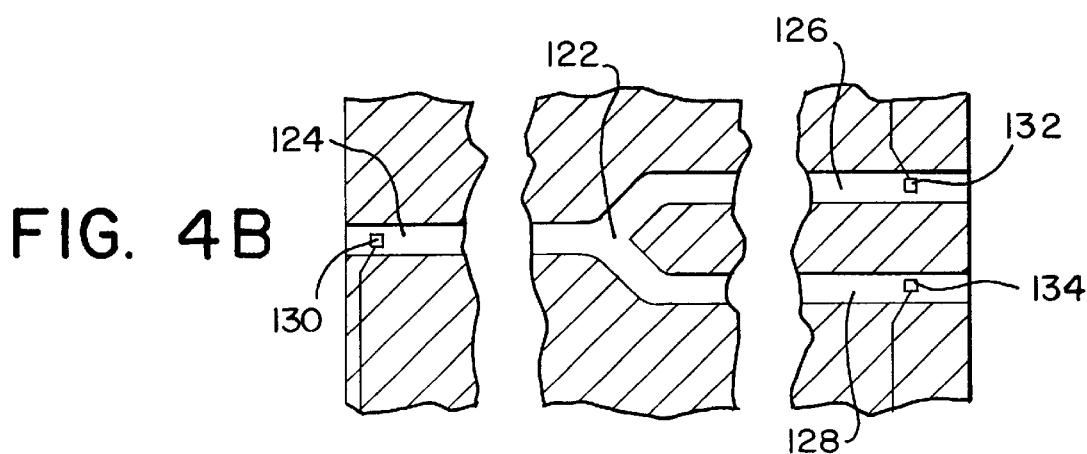
FIG. 4B shows another embodiment having electrodes disposed for electro-osmotic discrimination.

The discrimination region shown in FIG. 4B is suitable for use in a device that employs electro-osmotic flow, to move the cells and bulk solution through the device. FIG. 4B shows a discrimination region 122 which is preceded by a main channel 124. The main channel contains a junction that divides the main channel into two branch channels 126 and 128. An electrode 130 is placed downstream of the junction of the main channel, for example near the sample inlet of main channel. Electrodes are also placed in each branch channel (electrodes 132 and 134). The electrode 130 can be negative and electrodes 132 and 134 can be positive (or vice versa) to establish bulk solution flow according to well-established principles of electro-osmotic flow (25).

After a cell passes the detection region (not shown) and enters the discrimination region 122 (e.g. between the main channel and the two branch channels) the voltage to one of the electrodes 132 or 134 can be shut off, leaving a single attractive force that acts on the solution and the cell to influence it into the selected branch channel. As above, the appropriate electrodes are activated after the cell has committed to the selected branch channel in order to continue bulk flow through both channels. In one embodiment, the electrodes are charged to divert the bulk flow of cells into one branch channel, for example channel 126, which can be called a waste channel. In response to a signal indicating that a cell has been identified or selected for collection, the charge on the electrodes can be changed to divert the selected sell into the other channel (channel 128), which can be called a collection channel.

Figure 4C:
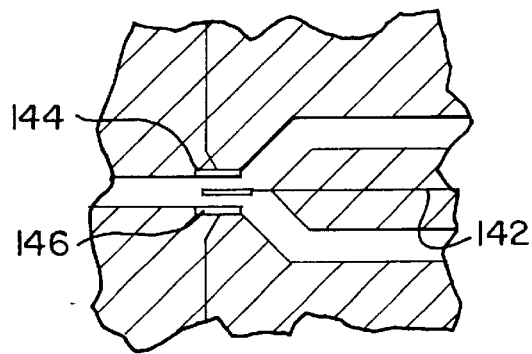
FIGS. 4C and 4D show two additional embodiments having valves disposed for pressure electrophoretic separation, where the valves are within the branch point, as shown in FIG. 4C, or within the branch channels, as shown in FIG. 4D.

In another embodiment of the invention, shown in FIG. 4C, the cells are directed into a predetermined branch channel via a valve 140 in the discrimination region. The valve 140 comprises a thin extension of material to which a charge can be applied via an electrode lead 142. The valve 140 is shown with both channels open, and can be deflected to close either branch channel by application of a voltage across electrodes 144 and 146. A cell is detected and chosen for sorting in the detection region (not shown), and can be directed to the appropriate channel by closing off the other channel, e.g. by applying, removing or changing a voltage applied to the electrodes. The valve can also be configured to close one channel in the presence of a voltage, and to close the other channel in the absence of a voltage.

Figure 4D:
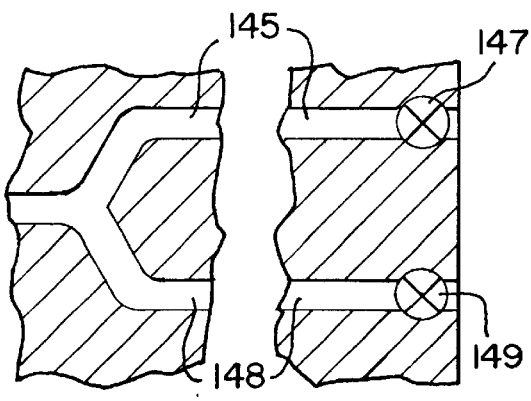

FIG. 4D shows another embodiment of a discrimination region of the invention, which uses flow stoppage in one or more branch channels as the discrimination means. The sample solution moves through the device by application of positive pressure at an end where the solution inlet is located. Discrimination or routing of the cells is affected by simply blocking a branch channel (145 or 148) or a branch channel sample outlet using valves in a pressure-driven flow (147 or 149). Due to the small size scale of the channels and the incompressibility of liquids, blocking the solution flow creates an effective "plug" in the non-selected branch channel, thereby temporarily routing the cell together with the bulk solution flow into the selected channel. Valve structures can be incorporated downstream from the discrimination region, which are controlled by the detection region, as described herein.

Alternatively, the discrimination function represented in FIG. 4D may be controlled by changing the hydrostatic pressure at the sample outlets of one or both branch channels 145 or 148. If the branch channels in a particular analysis unit have the same resistance to fluid flow, and the pressure at the sample inlet of the main channel of an analysis unit is P, then the fluid flow out of any selected branch channel can be stopped by applying a pressure P/n at the sample outlet of the desired branch channel, where n is the number of branch channels in the analysis unit. Accordingly, in an analysis unit having two branch channels, the pressure applied at the outlet of the branch to be blocked is P/2.

As shown in FIG. 4D, a valve is situated within each branch channel, rather than at the branch point, to close off and terminate pressurized flow through selected channels. Because the valves are located at a point downstream from the discrimination region, the channels in this region may be formed having a greater width than in the discrimination region in order to simplify the formation of valves. The width of the cantilever or diaphragm should approximately equal the width of the channel, allowing for movement within the channel. If desired, the element may be coated with a more malleable material, such as a metal, to allow for a better seal. Such coating may also be employed to render a non-conductive material, such as silicon dioxide, conductive. As above, suitable electrical contacts are provided for displacing the cantilever or diaphragm towards the opposing surface of the channel. When the upper surface is a glass cover plate, electrodes and contacts may be deposited onto the glass.

Figure 5:
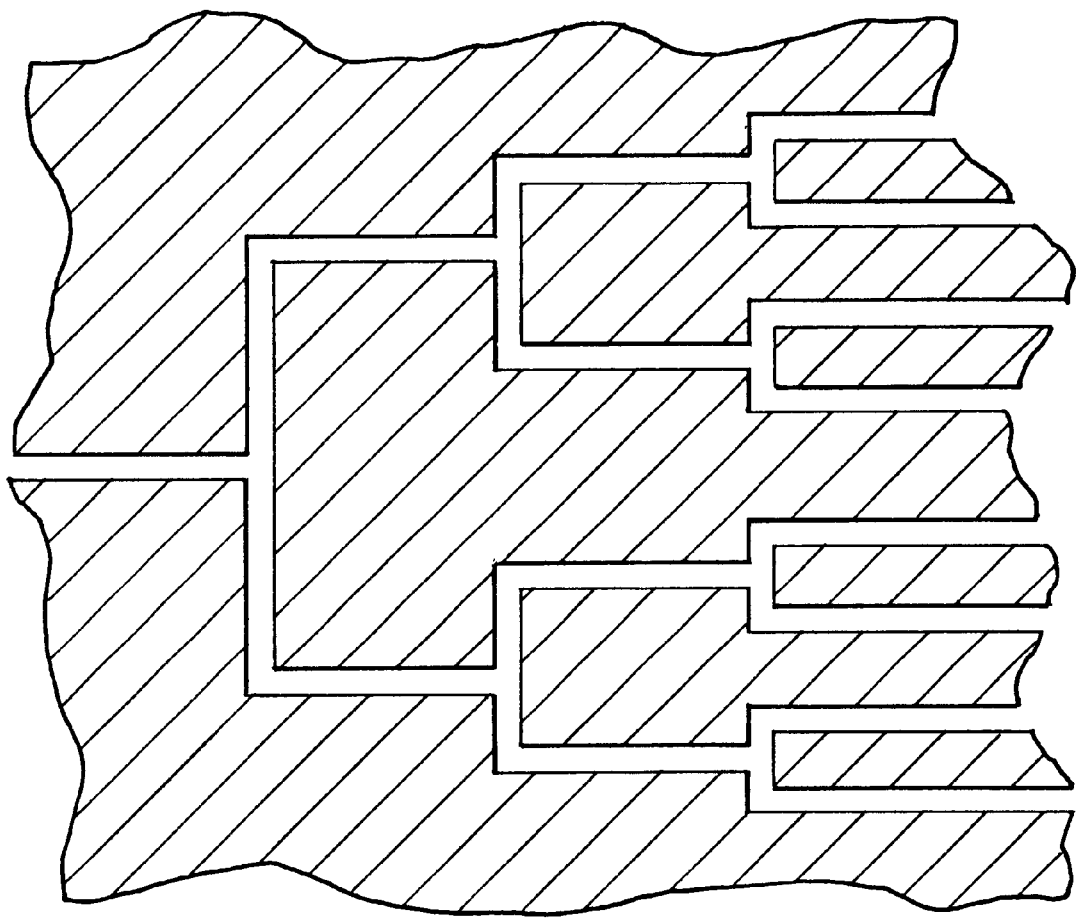
FIG. 5 shows a device with analysis units containing a cascade of detection and discrimination regions suitable for successive rounds of cell sorting.

FIG. 5 shows a device with analysis units containing a cascade of detection and discrimination regions suitable for successive rounds of cell sorting. For example, such a cascade configuration may be used to sequentially assay the cells for at least three different reporters, e.g., fluorescent dyes, corresponding to expression of at least three different cellular characteristics (markers). Samples collected at the outlet region of the different branch channels contain pools of cells expressing defined levels of each of the three markers. The number of reporters employed, and therefore the number of expressed markers of interest, can be varied to meet the needs of the practitioner.

Example 5

Reporters and Labels for Cell Sorting

To sort cells of the invention, cells are labeled with an optically detectable reporter which is analyzed and interpreted to determine whether the cell having the reporter should be sorted. The reporter may function in a variety of ways to effectively emit or display a readable signal that can be detected by the detection region.

In one embodiment the signal is in the form of a marker that associates within or binds to a particular cell type. The signal therefore acts to identify the cell as having a particular characteristic, e.g., a protein (receptor) or saccharride, such that the reporter signal from a given cell is proportional to the amount of a particular characteristic. For example, the reporter may be an antibody, a receptor or a ligand to a receptor (which bind to a protein or sugar), or a fragment thereof, each having a detectable moiety, such as a dye that fluoresces. The reporter can bind to a structure on the surface or within the cell of interest, and since the antibody contains a detectable reporter, any cell to which the reporter is bound would be detectable by the detection region of the device as the cell flows past such region. It should be appreciated by those having ordinary skill in the art that the antibody, receptor, ligand, or other agent that can act as a marker, can be modified to meet the needs of the practitioner, e.g., such as using fragments or making chimerics.

Fluorescent dyes are examples of optically-detectable reporters. There are a number of known dyes which selectively bind to nucleic acids, proteins and sugars. For DNA and RNA studies, these include, but are not limited to, Hoechst 33258, Hoechst 33342, DAPI (4',6-diamidino-2-phenylindole HCl), propidium iodide, dihydroethidium, acridine orange, ethidium bromide, ethidium homodimers (e.g., EthD-1, EthD-2), acridine-ethidium heterodimer (AEthD) and the thiazole orange derivatives PO-PRO, BOPRO, YO-PRO, To-PRO, as well as their dimeric analogs.POPO, BOBO, YOYO, and TOTO. All of these compounds can be obtained from Molecular Probes (Eugene, Oreg.). Extensive information on their spectral properties, use, and the like is provided in Haugland (30). Each dye binds at a known or empirically determined maximum density. Thus, by measuring the fluorescence intensity of a reporter molecule, the presence, concentration or relative amount of the desired cell characteristic can be determined, for example by comparison with an empirically determined reference standard. For example, one molecule of YOYO-1 has been found to bind 4–5 base pairs of DNA, and this ratio can be used to evaluate the length of an unknown DNA sequence, or to sort DNA based on a range or window of dye signal corresponding to a desired sorting length.

Ultraviolet reporters may also be used. Examples include green fluorescent protein and cascade blue.

Two applications of the invention are for the quantitation of cell surface and intracellular antigens, and of nucleic acid contents in cells, for the study of cellular differentiation and function, e.g. in the field of immunology and cancer cytology. For cellular surface antigen studies, phycobiliproteins, phycoerythrin, Texas Red and allophycocyanin, can be used as fluorescent labels for monoclonal antibodies for identification of blood cells and cancer cells. For cellular DNA/RNA analysis, the dyes mentioned above can be used. For the study of cellular functions, chromogenic or fluorogenic substrates were first used in flow cytometry to detect and quantitate intracellular enzyme activities (e.g., 4-Nitrophenyl, 5-Bromo-5-chloro-3-indolyl, fluorescein digalactoside, fluorescein diglucuronide, fluorescein diphosphate, and creatine phosphate.) These reporters can be used in the invention.

Dyes and fluorescent substrates for detection of other cellular functions such as protein contents (dyes e.g., fluorescein isothoiocyanate, sulphorhodamine, sulfosuccinimidyl esters, fluorescein-5-maleimide), intracellular pH (such as carboxyfluorescein and its derivative esters, and fluorescein sulfonic acid and its derivative diacetate), for signal transduction (e.g., fluorescent bisindolylmaleimides, hypericin, hypocrellin, forskolin) cytoplasmic and mitochondrial membrane potentials developed for analysis of cellular activation processes can also be used. Other applications suitable for use in the invention include chromogenic or fluoregenic probes for analysis of other cellular or encapsulating environments, such as detection of organelles (e.g. the mitochondria, lysosomes), cell morphology, cell viability and proliferation, receptors and ion channels, and for measurements of certain ions (e.g. metal ions, $Ca^{2+}$, $Mg^{2+}$, $Zn^{2+}$) in the cells or in the environment. Probes of the kinds described here be obtained for example from Molecular Probes (Eugene, Oreg.).

In another embodiment, cells may produce a reporter in vivo (e.g. a fluorescent compound) through interaction with a reagent added to the fluid medium. For example, cells containing a gene for an oxygenase enzyme may catalyze a reaction on an aromatic substrate (e.g. benzene or naphthalene) with the net result that the fluorescence, or another detectable property of the substrate, will change. This change can be detected in the detection region, and cells having that change in fluorescence can be collected based on predetermined criteria. For example, cells that produce a desired monooxygenase enzyme (such as a P450 enzyme) can be detected in the presence of a suitable substrate (such as naphthalene), and can be collected according to the invention, based on the ability of the enzyme to catalyze a reaction in which a detectable (e.g. fluorescent) product is produced from the substrate. Sorting can also be done based on a threshold or window concentration of reaction product, which in turn can be correlated with the level of fluorescence. A second reagent or coupling enzyme can be used to enhance fluorescence. See, Affholter and Arnold (50) and Joo et al. (51). Any mechanism of this kind, including any reporter or combinations of substrate, enzyme and product can be used for detection and sorting in a like manner, so long as there is at least one way to detect or measure the presence or degree of the reaction of interest.

The invention may be used to sort any prokaryotic (e.g., bacteria) or eukaryotic cells (e.g., mammalian, including human blood cells, such as human peripheral blood mononuclear cells (PBMCs)) which has a detectable characteristic or marker, or which can be labeled with a detectable reporter, for example an optically-detectable label. For example, antibodies or fragments thereof that recognize a receptor or antigen of interest, and which are linked to a fluorescent dye can be used to label cells. Examples of antigens which can be labeled with antibodies for cell sorting include, without limitation, HLA DR, CD3, CD4, CD8, CD11a, CD11c, CD14, CD16, CD20, CD45, CD45RA, and CD62L. The antibodies can in turn be detected using an optically-detectable reporter (either via directly conjugated reporters or via labeled secondary antibodies) according to methods known in the art. Alternatively, a ligand that is bound with a fluorescent dye and has affinity for a particular antigen or receptor of interest can be used in the same manner.

It will be appreciated that the cell sorting device and method described above can be used simultaneously with multiple optically-detectable reporters having distinct optical properties. For example, the fluorescent dyes fluorescein (FITC), phycoerythrin (PE), and "CYCHROME" (Cy5-PE) can be used simultaneously due to their different excitation and emission spectra. The different dyes may be assayed, for example, at successive detection and discrimination regions. Such regions may be cascaded as shown in FIG. 5 to provide samples of cells having a selected amount of signal from each dye.

Optical reporters, such as fluorescent moieties, can be excited to emit light of characteristic wavelengths by an excitation light source. Fluorescent moieties have an advantage in that each molecule can emit a large number of photons to a distance of 10 feet in response to radiation stimulus. Other optically detectable reporter labels include chemiluminescent and radioactive moieties, which can be used without an excitation light source. In another embodiment, absorbance at a particular wavelength, or measuring the index refraction of a particle, such as a cell, can be used to detect a characteristic. For example, if using an index of refraction, different types of cells can be distinguished by comparing differences in their retractive properties as they pass a light source.

Example 6

Operation of a Microfabricated Cell Sorting Device.

In operation of the microfabricated device of the invention, it is advantageous and preferred, to "hydrate" the device (i.e., fill the channels of the device with a solvent, such as water or the buffer solution in which the cells will be suspended) prior to introducing the cell-containing solution. Hydration of the device can be achieved by supplying the solvent to the device reservoir and applying hydrostatic pressure to force the fluid through the analysis unit(s).

Following the hydration step, the cell-containing solution is introduced into the sample inlets of the analysis unit(s) of the device. The solution may be conveniently introduced in a variety of ways, including by an opening in the floor of the inlet channel, reservoir (well) or via a connector. As a stream of cells to be sorted for a detectable characteristic or reporter is moved through the detection region, a signal from each cell is detected or measured and is compared with a threshold or set range of values to determine whether the cell possesses the desired characteristic based on the amount of reporter detected. The cells preferably move in single file.

Figure 2B:
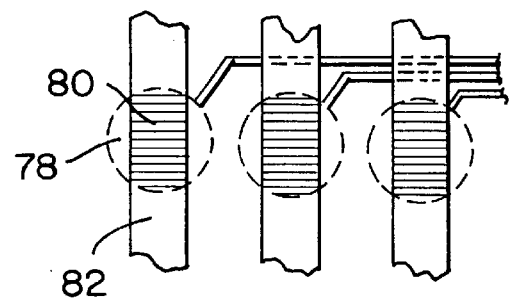
FIG. 2B shows another embodiment of a detection region, having an integrated photodiode detector, and providing a larger detection volume than the embodiment of FIG. 2A.

In the embodiment of this example, the level of reporter signal is measured at the detection region using an optical detector, which may include one or more of a photodiode (e.g., avalanche photodiode), a fiber-optic light guide leading, for example, to a photomultiplier tube, a microscope with a high numerical aperture objective and an intensified video camera, such as a CCD camera, or the like. The optical detector may be microfabricated or placed onto a cell analysis chip (e.g., a photodiode as illustrated in FIGS. 2A and 2B), or it may be a separate element, such as a microscope objective.

If the optical detector is used as a separate element, it is generally advantageous to restrict the collection of signal from the detection region of a single analysis unit at a given time. It may also be advantageous to provide an automated means of scanning the laser beam relative to the cell analysis chip, scanning the emitted light over the detector, or using a multichannel detector. For example, the cell analysis chip can be secured to a movable mount (e.g., a motorized/computer-controlled micromanipulator) and scanned under the objective. A fluorescence microscope, which has the advantage of a built-in excitation light source (epifluorescence), is preferably employed for detection of a fluorescent reporter.

The signal collected from the optical detector is routed, e.g., via electrical traces and pins on the chip, to a processor, which interprets the signals into values corresponding to the cell type characteristic giving rise to the signal. These values are then compared, by the processor, with pre-loaded instructions containing information about which branch channel the cells having the desired characteristic will be routed. In some embodiments there is a signal delay period (i.e., long enough to allow the reporter signal from the cell to reach the discrimination region), after which the processor sends a signal to actuate the active elements in the discrimination region to route the cell into the appropriate branch channel. In other embodiments there is little or no signal delay period, because the detection region is immediately adjacent to the branch point, and switching can be immediate. There may be a sorting delay period, which is the time needed to ensure that a selected cell is sorted into the correct branch channel, i.e. before switching back to normal (nonselected) flow. This period can be empirically determined.

Any needed or desired delay period can be readily determined according to the rate at which the cells move through the channel, i.e. their velocity, and the length of the channel between the detection region and the discrimination region. In addition, depending on the mechanism of flow, cell size may also affect the movement (velocity) through the device. In cases where the sample solution is moved through the device using hydrostatic pressure (e.g., as pressure at the inlet region and/or suction at the outlet regionend), the velocity is typically the flow rate of the solution. If the cells are directed through the device using some other force, such as electro-osmotic flow (e.g. using an electric field or gradient between the inlet region and the outlet region), then the delay period is a function of velocity and cell size, and can be determined empirically by running standards including different sizes or types of known cells. Thus, the device can be appropriately calibrated for the intended use.

The time required to isolate a desired quantity of cells depends on a number of factors, including the size of the cells, the rate at which each analysis unit can process the individual fragments, and the number of analysis units per chip. The time required can be calculated using known formulas. For example, a chip containing 1000 analysis units, each of which can sort 1,000 cells per second, could isolate about 100 $\mu$g of 3 $\mu$m cells in about 1 hour.

The concentration of cells in the sample solution can influence sorting efficiency, and can be optimized. The cell concentration should be dilute enough so that most of the cells pass through the detection region one by one (in single file), with only a small statistical chance that two or more cells pass through the region simultaneously. This is to insure that for the large majority of measurements, the level of reporter measured in the detection region corresponds to a single cell and not two or more cells.

The parameters which govern this relationship are the volume of the detection region and the concentration of cells in the sample solution. The probability that the detection region will contain two or more cells ($P_{\geq 2}$) can be expressed as $$P_{\geq 2}=1-\{1+[\text{cell}]\times V\}\times e^{-[\text{cell}]\times V}$$

where [cell] is the concentration of cells in units of cells per $\mu$m$^3$ and V is the volume of the detection region in units of $\mu$m$^3$.

It will be appreciated that $P_{\geq 2}$ can be minimized by decreasing the concentration of cells in the sample solution. However, decreasing the concentration of cells in the sample solution also results in an increased volume of solution processed through the device and can result in longer run times. Accordingly, it is desirable to minimize the presence of multiple cells in the detection chamber (thereby increasing the accuracy of the sorting) and to reduce the volume of sample fluid thereby permitting a sorted sample in a reasonable time in a reasonable volume containing an acceptable concentration of cells.

The maximum tolerable $P_{\geq 2}$ depends on the desired "purity" of the sorted sample. The "purity" in this case refers to the fraction of sorted cells that are in a specified size range, and is inversely proportional to $P_{\geq 2}$. For example, in applications where high purity is not needed or desired a relatively high $P_{\geq 2}$ (e.g., $P_{\geq 2}$=0.2) may be acceptable. For most applications, maintaining $P_{\geq 2}$ at or below about 0.1, preferably at or below about 0.01, provides satisfactory results.

For example, where $P_{\geq 2}$ is 0.1, it is expected that in about 10% of measurements, the signal from the detection region is a result of the presence of two or more cells. If the total signal from these cells is in the range corresponding to a value set for a desired cell type, those cells will be sorted into the channel or tube predetermined for the desired cell type.

The cell concentration needed to achieve a particular $P_{\geq 2}$ value in a particular detection volume can be calculated from the above equation. For example, a detection region in the shape of a cube 10 microns per side has a volume of 1 pl. A concentration of cells which have a diameter of 1 micron, resulting on average in one cell per pl, is about 1.7 pM. Using a $P_{\geq 2}$ value of about 0.01, the cell concentration in a sample analyzed or processed using the 1 pl detection region volume is approximately 10 pM, or roughly one cell per 3 detection volumes ([cell]×V=~0.3). If the concentration of cells is such that [cell]×V is 0.1, then $P_{\geq 2}$ is less than 0.005; i.e., there is less than a one half of one percent (0.5%) chance that the detection region will, at any given time, contain two or more cells.

As discussed above, the sample mixture introduced into a device of the invention should be dilute enough such that there is a high likelihood that only a single cell will occupy the detection region at any given time. This will allow the cells to be in "single file", separated by stretches of cell-free solution as the solution flows through the device between the detection and discrimination regions. The length of the channel, discussed above, between the detection and discrimination region should therefore not be too long, such that random thermal diffusion does not substantially alter the spacing between the cells. In particular, the channel length should be short enough so that a cell can traverse it in short enough time, such that even the smallest cells being analyzed will typically be unable to diffuse and change position or order in the line of cells. The channel should also be long enough so that flow control can be switched in time to appropriately divert a selected cell in response to detection or measurement of a signal produced from examination of the cell as it passes through the detection region.

The diffusion constant of a 0.5 m sphere is approximately 5×10$^{-9}$ cm$^2$/sec. The diffusion equation gives the distance (x) that the sphere will diffuse in time (t) as: $<x^2>=Dt$, where D is the diffusion constant given by $D=k_BT/6\pi\eta R_0$. In this equation, $k_b$ is the Boltzmann's Constant, T is the temperature, $\eta$ is the viscosity of the fluid and $R_0$ is the diameter of the sphere. Using this relationship, it will be appreciated that a 0.5 $\mu$m cell takes about 50 seconds to diffuse 500 $\mu$m. The average spacing of cells in the channel is a function of the cross-sectional area of the channel and the cell concentration, the latter typically determined in view of acceptable values of $P_{\geq 2}$, discussed above. From these relationships, it is then easy to calculate the maximum channel length between the detection and discrimination region which would ensure that cells do not change order or position in the line of cells. In practice, the channel length between the detection and discrimination regions is between about 1 $\mu$m and about 100 $\mu$m.

Shear forces may affect the velocity at which the cells move through the microfluidic device, particularly when living cells are to be sorted and collected. Experiments have shown that high electric fields, in the range of 2–4 kV/cm for human erythrocytes and 5–10 kV/cm for yeast cells can be used to introduce DNA and other substances into cells using electroporation. At these voltages there was no cell lysis, although membrane permeation was possible. To avoid membrane permeation and cell lysis, it is preferred that the electric fields applied to move cells in any of the described flow techniques is less than about 600 V/cm and most preferably less than about 100 V/cm.

Example 7

Elastomeric Microfabricated FACS

This Example demonstrates the manufacture and operation of a disposable microfabricated FACS device, which can function as a stand-alone device or as a component of an integrated microanalytical chip, in sorting cells or biological materials. The device permits high sensitivity, no cross-contamination, lower cost to operate and manufacture than conventional FACS machines and multiple-hour run times. In this example, the microfabricated chip had a detection volume of approximately 250 fl and single channel throughput of about 20 cells/second. The device obtained substantial enrichment of micron-sized fluorescent bead populations of different colors. In addition, populations of $E.\ coli$ cells expressing green fluorescent protein were separated, and enriched, from a background of non-fluorescent (wild type) $E.\ coli$ cells. The bacteria were also found to be viable after extraction from the sorting device.

Preparation of the Microfabricated Device

A silicon wafer was etched and fabricated as described above and in (15). After standard contact photolithography techniques to pattern the oxide surface of the silicon wafer, a $C_2F_2/CHF_3$ gas mixture was used to etch the wafer by RIE. The silicon wafer was then subjected to further etch with KOH to expose the silicon underneath the oxide layer, thereby forming a mold for the silicone elastomer. The silicon mold forms a "T" arrangement of channels. The dimensions of the channels may range broadly, having approximately 5×4 μm dimension.

Figure 6:
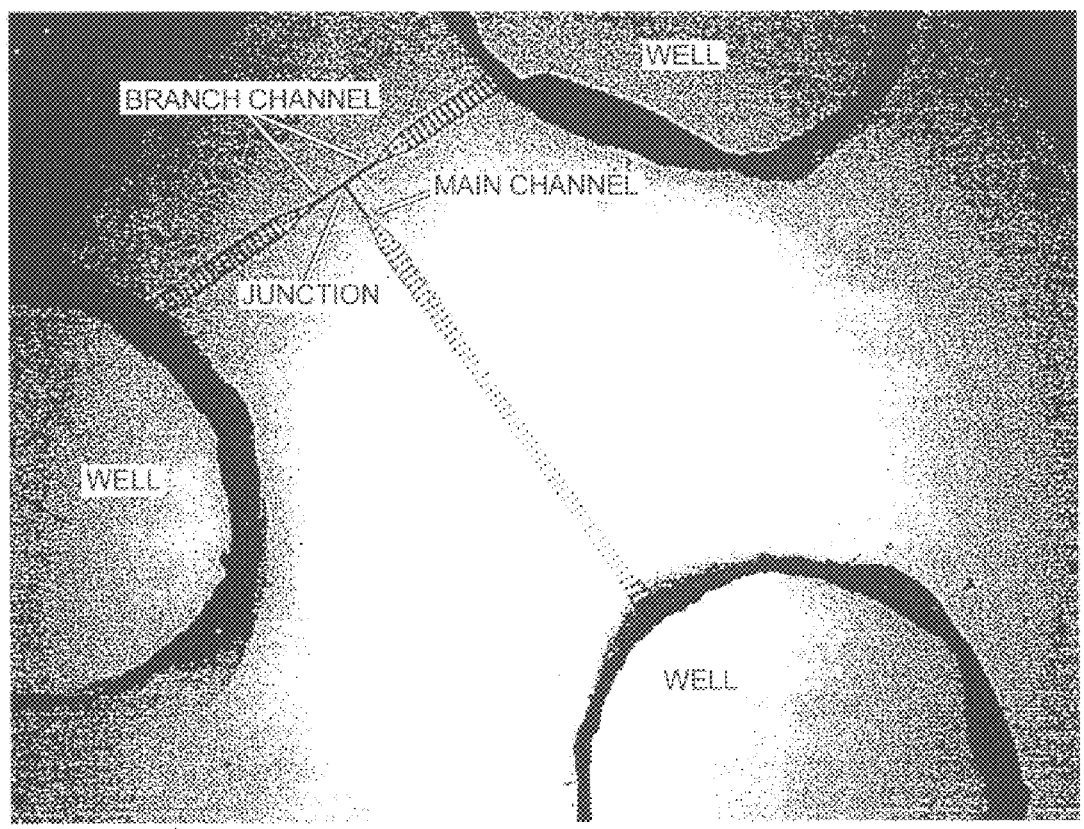
FIG. 6 is a photograph of an apparatus of the invention, showing a chip with an inlet channel and reservoir, a detection region, a branch point, and two outlet channels with reservoirs.

A representative device of the invention is shown in FIG. 6. The etching process is shown schematically in FIG. 7. Standard micromachining techniques were used to create a negative master mold out of a silicon wafer. The disposable silicone elastomer chip was made by mixing General Electric RTV 615 components (20) together and pouring onto the etched silicon wafer. After curing in an oven for two hours at 80° C., the elastomer was peeled from the wafer and bonded hermetically to a glass cover slip for sorting. To make the elastomer hydrophilic the elastomer chip was immersed in HCl (pH=2.7) at 60 degrees C. for 40 to 60 min. Alternatively, the surface could have been coated with polyurethane (3% w/v in 95% ethanol and diluted 10× in ethanol). It is noted that the master wafer can be reused indefinitely. The device shown has channels that are 100 μm wide at the wells, narrowing to 3 μm at the sorting junction (discrimination region). The channel depth is 4 μm, and the wells are 2 mm in diameter.

Figure 7:
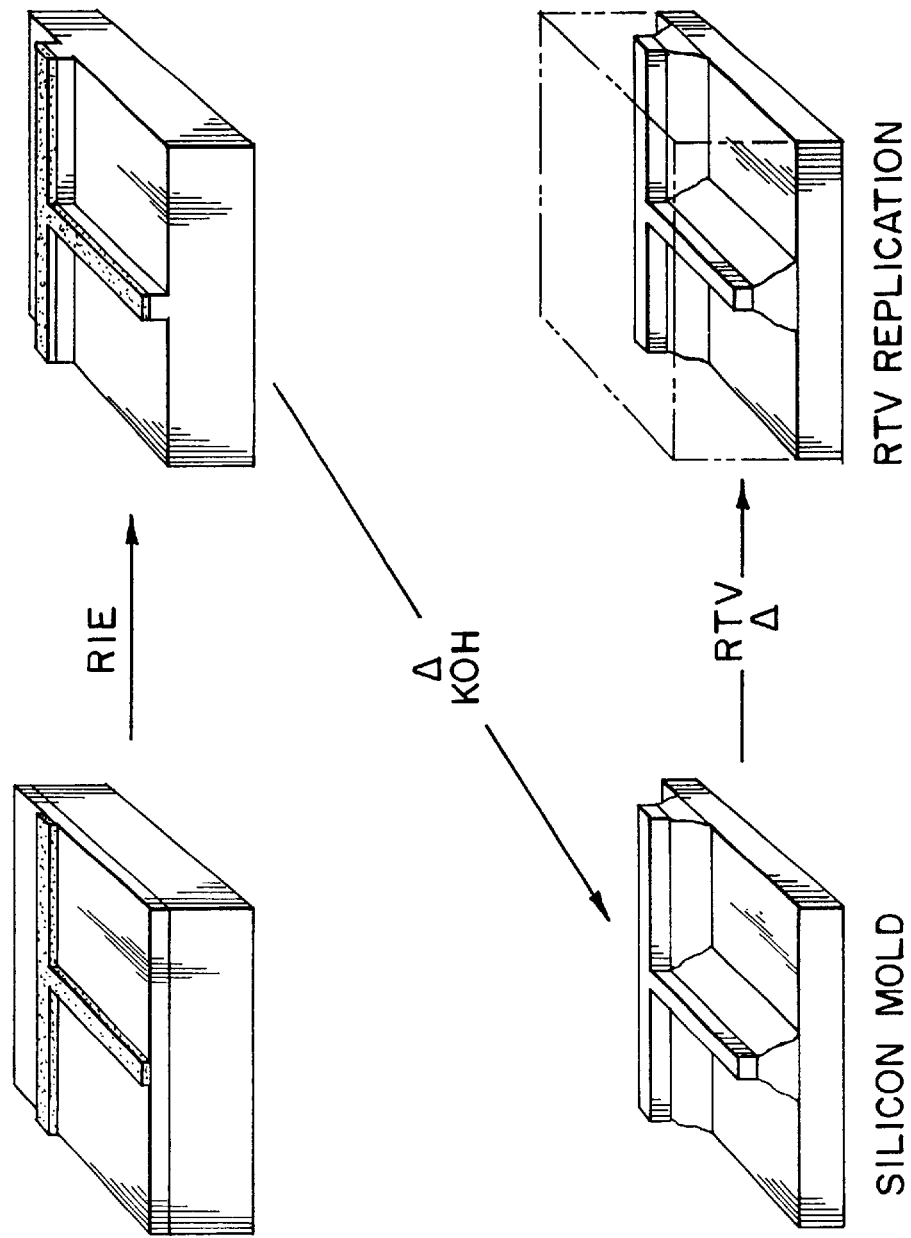
FIG. 7 shows a schematic representation of a process for obtaining a silicone elastomer impression of a silicon mold to provide a microfabricated chip according to the invention.
Figure 8:
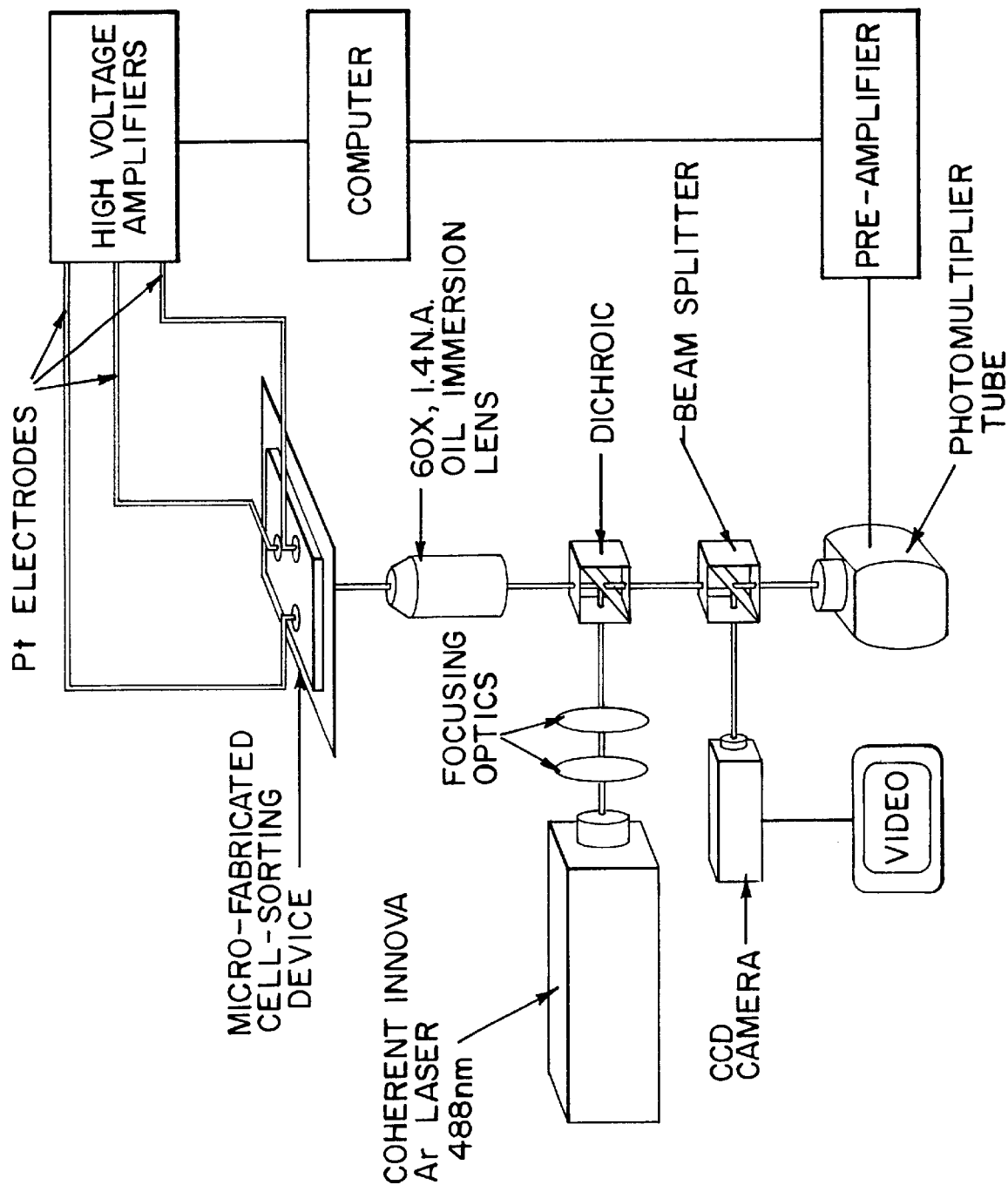
FIG. 8 shows a schematic representation of an apparatus of the invention, in which a silicone elastomer chip is mounted on an inverted microscope for optical detection of a laser-stimulated reporter. Electrodes are used to direct cells in response to the microscope detection.

In this embodiment the cell-sorting device was mounted on an inverted optical microscope (Zeiss Axiovert 35) as shown in FIG. 8. In this system, the flow control can be provided by voltage electrodes for electro-osmotic control or by capillaries for pressure-driven control. The detection system can be photomultiplier tubes or photodiodes, depending upon the application. The inlet well and two collection wells were incorporated into the elastomer chip on three sides of the "T" forming three channels (FIGS. 6 and 7). The chip was adhered to a glass coverslip and mounted onto the microscope.

Three platinum electrodes were each inserted into separate wells. A water-cooled argon laser (for cells) or a 100 W mercury lamp (for beads) focused through an oil immersion objective (Olympus Plan Apo 60×1.4NA) was used to excite the fluorescence and a charge-coupled device (CCD) camera took the image. To select for red fluorescence emission a 630 nm±30 emission filter (Chroma) is used. The detection region was approximately 5 to 10 μm below the T-junction and has a window of approximately 15×5 μm dimension. The window is, implemented with a Zeiss adjustable slit. Using one or two Hammatzu R928 photomultiplier tubes (bias −850V) with custom current-to-voltage amplifier, or using photodiodes, as detectors, and using different emission filters (depending on the fluorescence), photocurrent(s) from the detector(s) were converted to voltage by a Burr-Brown OP128 optical amplifier ($10^7$V/A), digitized by National Instrument PC1200 board and processed into a computer. The voltages on the electrodes are provided by a pair of Apex PA42 HV op amps powered by Acopian power supplies. The third electrode was ground. Adjusting the voltage settings on the PC1200 board analog outlets and its amplification to the platinum electrodes can control the switching of the directions of the fluids. Thus, cells can be directed to either side of the "T" channel's depending upon the voltage potential settings. Furthermore; different ways of sorting in the microfluidic device can be achieved by different computer programs, e.g., different computer-controlled procedures using known programming techniques.

Sorting Experiments

Figure 9:
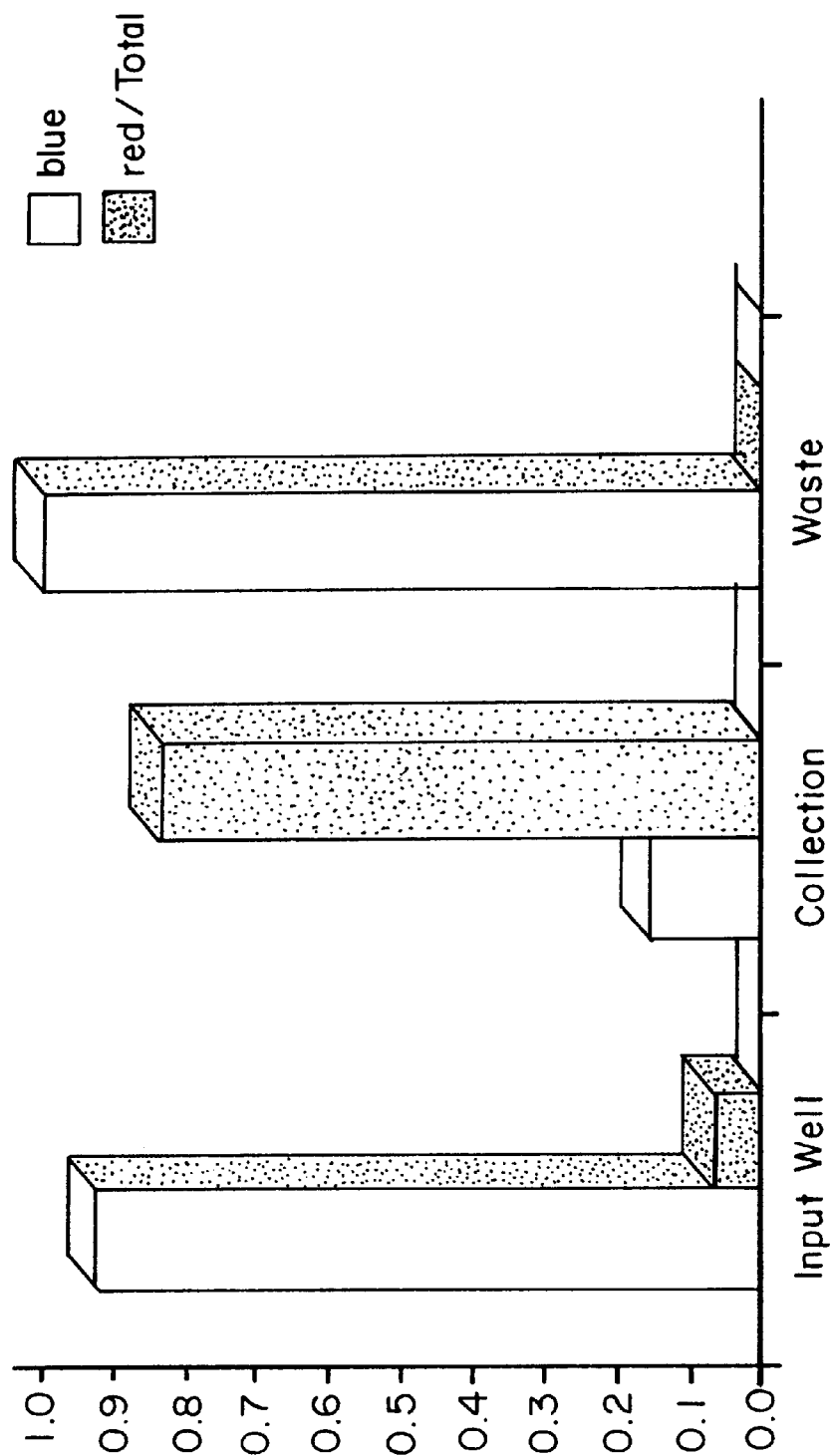
FIG. 9 shows the results of sorting blue and red fluorescent beads having an initial ratio of 10:1, respectively, using a forward mode. The darker bar represents the ratio of red beads over the total number of beads sorted and the lighter bar represents the ratio of blue beads over the total number of beads sorted.
Figure 10:
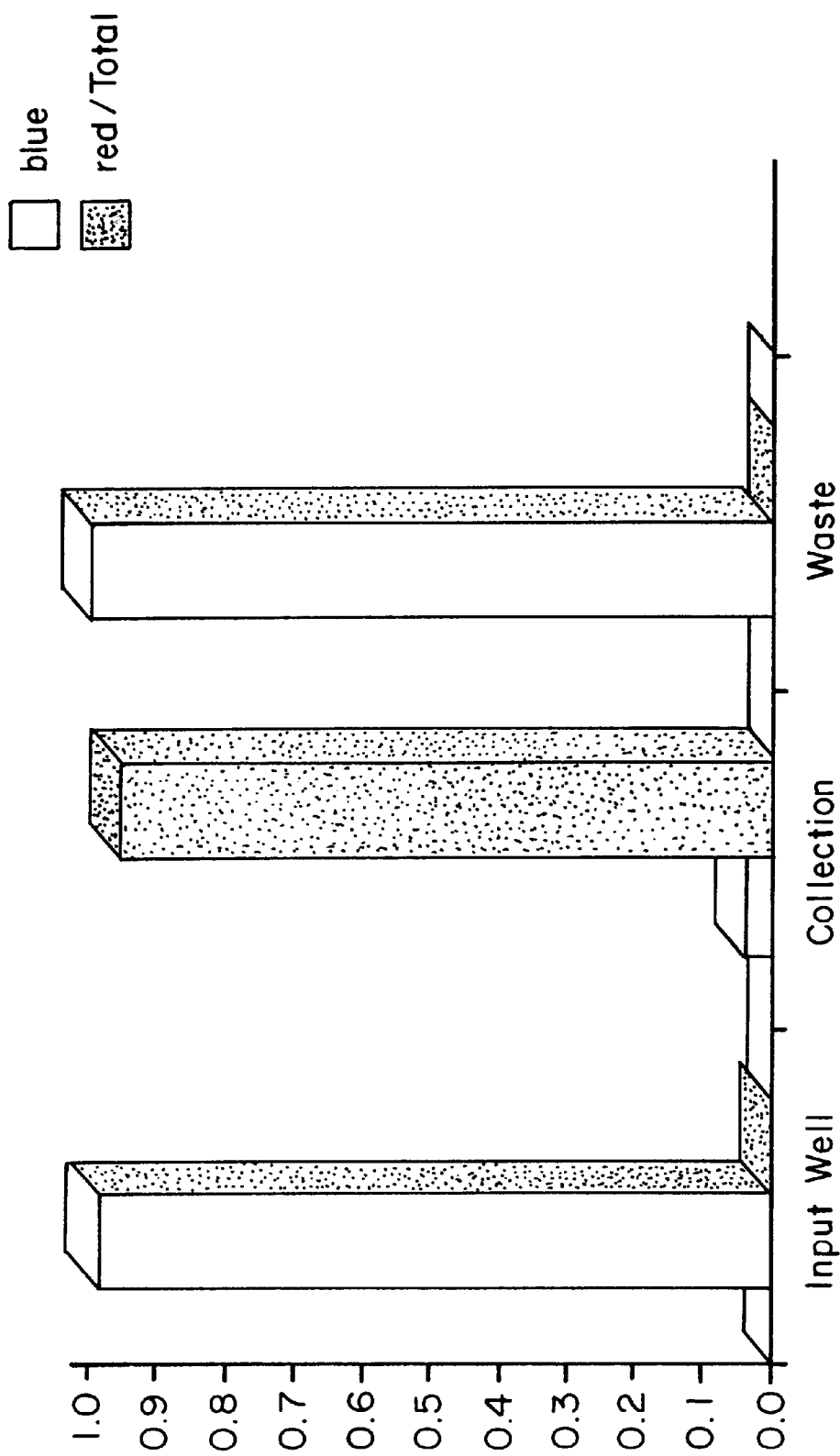
FIG. 10 shows the results of sorting blue and red fluorescent beads having an initial ratio of 100:1, respectively, using a reversible switching mode. The darker bar represents the ratio of red beads over the total number of beads sorted and the lighter bar represents the ratio of blue beads over the total number of beads sorted.
Figure 11:
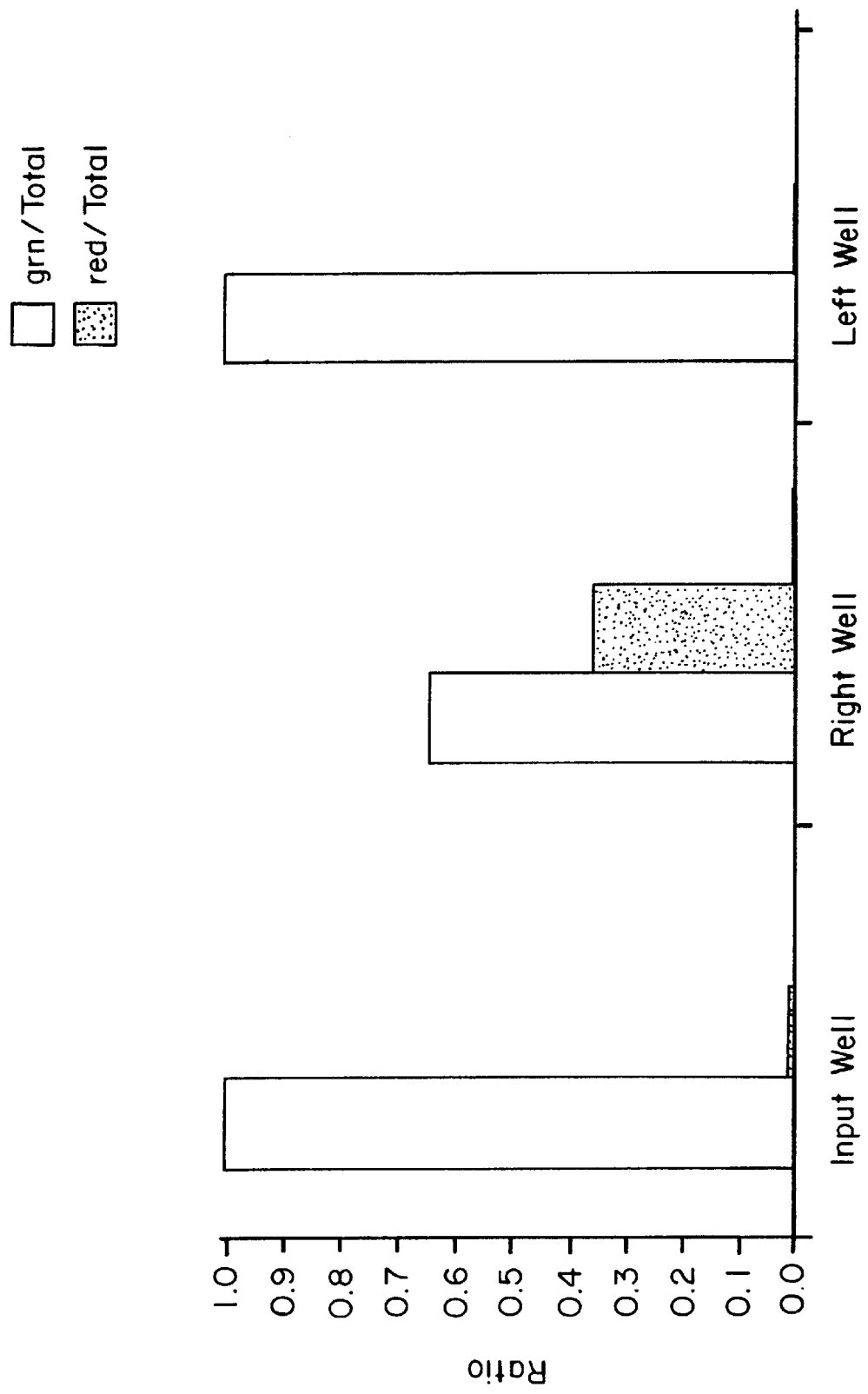
FIG. 11 shows the results of sorting green and red fluorescent beads having an initial ratio of 100:1, respectively, using a reversible switching mode. The darker bar represents the ratio of red beads over the total number of beads sorted and the lighter bar represents the ratio of green beads over the total number of beads sorted.

This embodiment of the microfabricated FACS system was used to sort fluorescent beads of different emission wavelengths in different ratios up to 33,000 beads per hour throughput (See FIGS. 9–11). Extra reservoir wells were incorporated into the outer side of the three wells of the chip in order to avoid ion-depletion, and platinum electrodes (with the ground electrode in the inlet well) were inserted into the reservoir wells. One micron diameter beads were suspended in PBS (137 mM NaCl, 2.7 mM KCl, 4.3 mM $Na_2HPO_4.7H_2O$, 1.4 mM $KH_2PO_4$) with 10% BSA (1 g/l) and 0.5% Tween 20 in various ratios and dilutions. Samples of the different colored fluorescent beads, having ratios as indicated below, were injected into the inlet well in 10 to 30 μl aliquots. The collection wells were filled with the same buffer.

To sort the beads the optical filter in front of the PMT passed only the color fluorescence corresponding to the color of the bead on interest, e.g., red fluorescent light to sort red beads. Voltages on the electrodes were set for switching purposes, either for sorting or reversible switching. The time duration of sorting can be as long as 3 hours, although the voltage settings may have to be readjusted from time to time. The coefficient of variation of bead intensity was measured as about 1 to 3% depending on the depth of the channel and the surface treatment of the elastomer. After sorting, enrichment of the beads was determined by the processor that recorded the data gathered by the detection region and was verified by counting.

In the following experiments, the channels of the microfabricated device were 3×4 with bead-sorting and 10×4 with cell-sorting.

A. Sorting green fluorescent beads from red fluorescent beads

As shown in FIG. 7, sorting of green fluorescent beads to red fluorescent beads in a ratio of 100:1 was performed. A mixture of 0.375% beads resuspended in 137 mM NaCl PBS with 10% BSA+0.5% Tw20 was put through the 3×4 μm silicone elastomer device of the invention for approximately 22 minutes. Using a mercury lamp as the light source, the R928 Hammatzu PMT bias was −850 V with 630 nm±30 emission filter.

B. Sorting red fluorescent beads from blue fluorescent in forward and reverse

FIG. 9 shows sorting of blue fluorescent beads to red fluorescent beads in a ratio of 10:1 using a forward mode. A mixture of 1.5% beads resuspended in 137 mM NaCl PBS with 10% BSA+0.5% Tw20 was sorted using a 3×4 µm device for about 24 minutes. Red beads were enriched 8.4 times. The darker and lighter bars represent the ratio of red or blue beads over the total number of beads sorted, respectively.

FIG. 10 shows the sorting of red fluorescent beads from blue fluorescent beads using a reversible mode. Beads were prepared in the buffer as described in a ratio of 100:1 (blue:red). After 6 min. the collection channel had a sample of red beads that had been enriched by 96 times. The darker and lighter bars represent the ratio of red or blue beads over the total number of beads sorted, respectively. The throughput was approximately 10 beads/s.

C. Sorting green fluorescent beads from red fluorescent in reversible mode

FIG. 11 shows the results of sorting, by reversible switching, green fluorescent beads to red fluorescent beads in a ratio of 100:1. A mixture of 0.375% beads resuspended in 137 mM NaCl PBS with 10% BSA+0.5% Tw20 was sorted using a 3×4 µm device for about 12 minutes. Reversible switching provides for a rapid and high throughput of undesired beads or cells, with a rapid reversal of fluid flow once a desired bead or cell is detected. This allows for a high throughput and reliable capture of rare cells or events, with rapid analysis of results. The data represented in FIG. 11 show that the red beads were enriched by about 36 times. The darker and lighter bars represent the ratio of red or green beads over the total number of beads sorted, respectively.

D. Sorting E. coli cells expressing green fluorescent protein from wild type cells Sorting results using E. coli cells demonstrated the enrichment capability of microfabricated FACS on living cells. E. coli cells (HB101) expressing green fluorescent protein (GFP) were grown at 30 degrees C. for 12 hours in LB+amp (one colony inoculated into 3 ml medium). The preparation of GPF-expressing E. coli cells is described for example in Sambrook et al. (48). Wild type E. coli HB101 cells were also incubated for 12 hours in LB only medium. After incubation, HB101 and GFP HB101 E. coli cells were resuspended in PBS (I=0.021) three times and stored at 4 degrees C. for sorting.

Immediately before sorting, the cells were resuspended again into PB (4.3 mM $Na_2HPO_4.7H_2O$, 1.4 mM $KH_2PO_4$) containing $10^{-5}$ to $10^{-4}$ M SDS and diluted 10 to 100 fold depending on the absorbance (1 to 1.5) and concentration of the cells. The cells were filtered through a 5 mm syringe filter (Millipore) for elimination of any elongated cells. Fluorescence was excited using a 488 nm Coherent Innova 70 argon ion laser (30 to 50 mW light source, 6 mW out of the objective), the R928 Hammatzu PMT bias was–850V (Chroma) and the emitted fluorescence was filtered using a 535±20 filter.

Different ratios of wildtype E. coli to GFP expressing E. coli cells (described below) were mixed and introduced into the inlet well of the device (volume ranges from 10 to 30 µl of sample); the collection wells were also filled with 10 to 30 µl of PB with $10^{-5}$ to $10^{-4}$ M SDS. After inserting the three platinum electrodes into the wells (with the ground electrode in the inlet well), the voltages were set for forward or reversible sorting modes. The default voltages here were set to –80V and –56V for the waste and collection channels respectively. After sorting for a about two hours, cells were collected using a pipette and streaked onto antibiotic-containing plates (LB plates) and incubated overnight at 37 degrees C for colony-counting.

Figure 12:
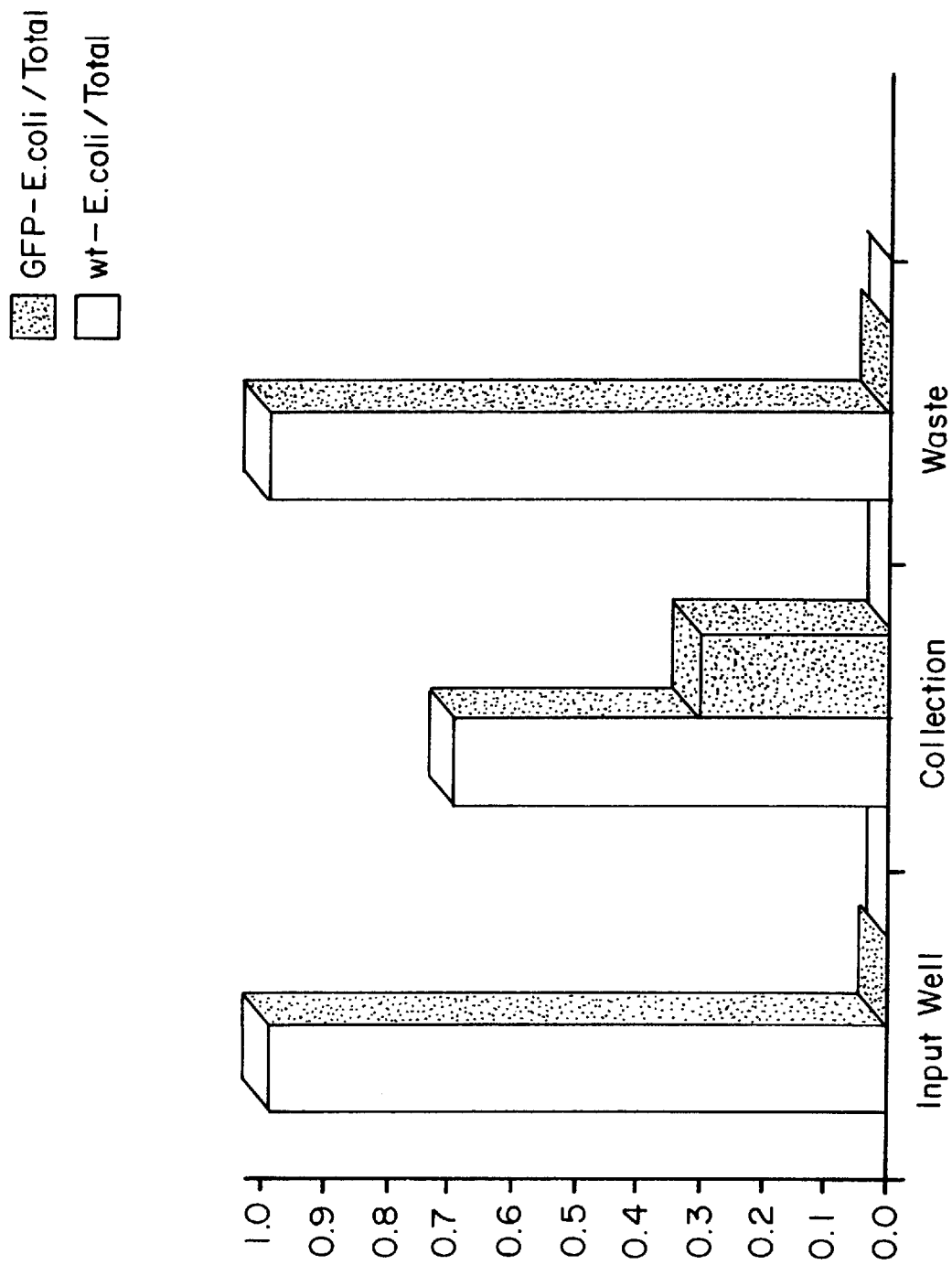
FIG. 12 shows the results of sorting wild-type (non-fluorescent) *E. coli* HB101 cells and *E. coli* HB101 cells expressing green fluorescent protein (GFP) having an initial ratio of 100:1, respectively, using a forward switching mode. The lighter bar represents the ratio of wildtype *E. coli* cells over the total number (approximately 120,000) of cells sorted and the darker bar represents the ratio of GFP-expressing *E. coli* cells over the total number of cells sorted.
Figure 13:
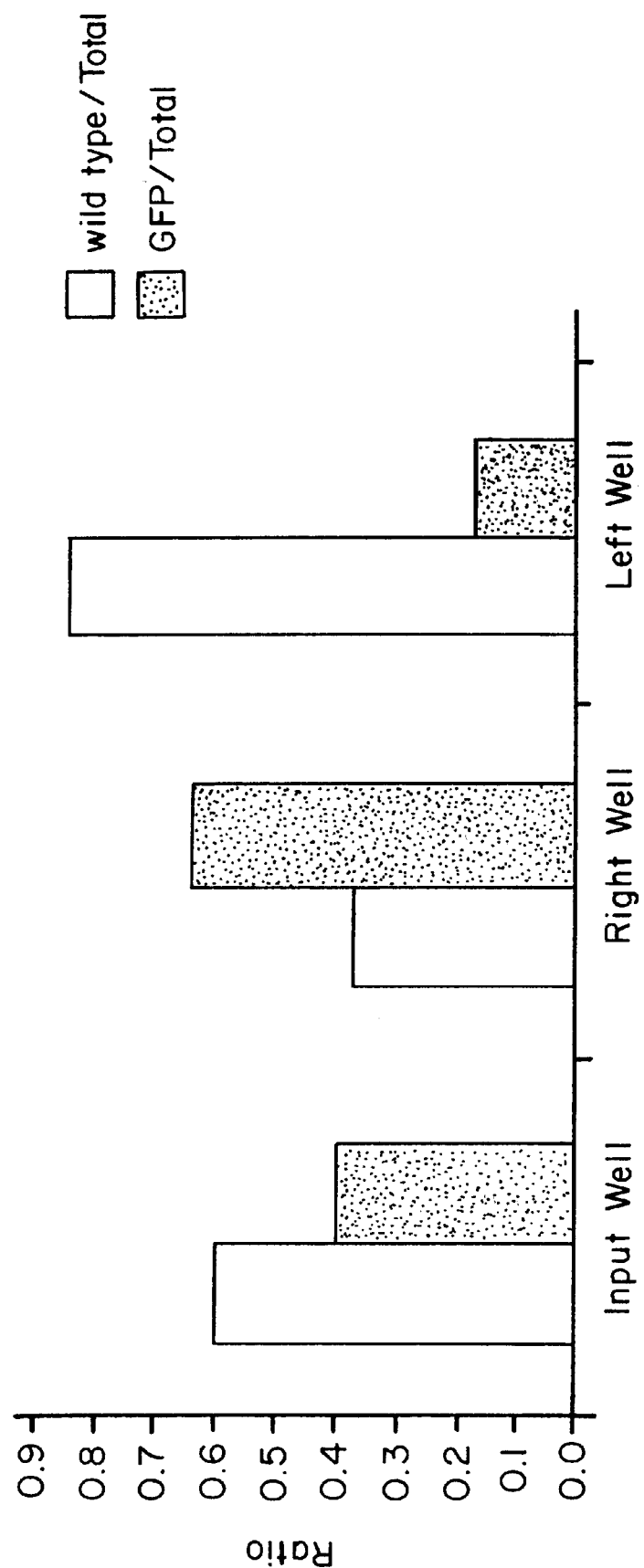
FIG. 13 shows the results of sorting wild-type (non-fluorescent) *E. coli* HB101 cells and *E. coli* HB101 cells expressing green fluorescent protein (GFP) having an initial ratio of 3:2, respectively, using a forward switching mode.

In a first experiment, the initial ratio of wild type to GFP-expressing E. coli cells was 100:1 (results in FIG. 12). After 2 hours of sorting the GFP E. coli cells recovered from the collection well were enriched 30 times, with yields of 20%. In FIG. 12, the dark and light bars represent the ratios of non-fluorescent wild type E. coli and GFP-expressing E. coli to the total number of cells sorted (approximately 120,000 cells), respectively. The sorted cells show relatively constant viability in electric fields up to about 100 V/cm, corresponding to velocities of about 1 to 3 mm/s. The throughput was about 20 cells/s, which can be improved, e.g., by adding a parallel device fabrication or pressure driven switching scheme. FIG. 13 shows the results from cell sorting wild type and GFP-expressing E. coli cells in an initial ratio of 3:2. The GFP-expressing E. coli were enriched by about 1.75 times.

Example 8

Sorting for Molecular Evolution

One preferred embodiment is for sorting microbial cells (bacteria, yeast, fungi) and particles containing genetic material for molecular evolution, also known as "directed evolution" (41). Directed evolution involves creating a set of mutated nucleic acid sequences followed by screening for those that alter or improve a predetermined characteristic (e.g. activity of an enzyme, productivity of a certain metabolite, or an activity associated with a particular gene or polynucleotide). The gene products are then created, either by inserting the genetic material in microbial cells and relying on the cellular machinery to create the gene products (proteins), or by transcribing the genetic material into protein using cell-free synthesis methods (42–45). The gene products are then screened to identify altered or improved sequences. If desired, these sequences can be isolated and further mutated in further cycles of evolution. After one or more cycles of evolution, gene products exhibiting the desired characteristics may be generated. It is also possible that the activity or property detected, e.g. the reporter, is associated with a particular polynucleotide sequence itself, and that the polynucleotide is a desired final product for which sorting is desired. In this case, the evolution can be performed in vitro (without cells) and without translating the polynucleotides into gene products.

The cell sorter of this invention can be used to screen the microbial cells to determine whether they exhibit the desired characteristics and therefore contain desired altered or improved genetic material. If cell-free protein synthesis has been used, i.e. without living biological cells, this synthesis apparatus, e.g. an RNA-protein fusion such as that described by Roberts & Szostak (45) or a cell-free synthesis system as in Jermutus (44), can be encapsulated into particles such as liposomes or a water-in-oil emulsion, Tawfik and Griffiths (47), for generation of the gene product and sorting. Polynucleotide libraries (DNA or RNA) can also be sorted in encapsulated form. The size of the particles for cell-free synthesis or polynucleotide evolution may be smaller than typical microbial cells: particles as small as 0.1 micron can be used, provided there is sufficient signal obtain in the detection region to allow detection of the desired particles (i.e. those exhibiting the desired characteristic) and their discrimination from the undesired particles.

For example, the goal of a directed evolution experiment may be to improve the activity of an enzyme in catalyzing a reaction on a particular substrate, or even to create a new enzyme that catalyzes this desired reaction. If the enzymatic reaction generates a fluorescent product, either directly through its interaction with the substrate, or indirectly (e.g. via other enzymes), the microbial host cells or particles will become fluorescent. Affholter (50) and Joo (51). The sorter can be used to sort those cells or particles exhibiting higher levels of fluorescence from those with lower levels, placing those with the high fluorescence levels in the collection well. The genetic material can be isolated from these cells or particles and subjected to amplification by PCR and further mutation, e.g. by PCR and/or in vitro recombination (DNA shuffling) as in Stemmer (46). This new material can be inserted into the host cells or particles to create the new gene products and sorted again, for as many generations as is required to achieve the desired properties.

Alternatively, the goal of a directed evolution experiment may be to discover a protein that binds to a particular target molecule. In this case the target molecule may be labeled with a reporter whose fluorescence properties change in a detectable fashion upon binding. Thus, if the cells contain the desired protein, they will be detected in the detection region of the invention, and collected accordingly. The cells can be biological cells that produce the protein, or particles encapsulating the genes and cell-free protein synthesis apparatus. The final product or desired result may be a polynucleotide, and not a protein, in which case there is no need for protein synthesis machinery. Thus, in suitable applications, binding or catalysis can be detected or measured directly, using appropriate reporters as described.

Example 9

Exemplary Embodiment and Additional Parameters
Microfluidic Chip Fabrication

In a preferred embodiment, the invention provides a "T" on "Y" shaped series of channels molded into optically transparent silicone rubber or PolyDiMethylSiloxane (PDMS), preferably PDMS. This is cast from a mold made by etching the negative image of these channels into the same type of crystalline silicon wafer used in semiconductor fabrication. As described above, the same techniques for patterning semiconductor features are used to form the pattern of the channels. The uncured liquid silicone rubber is poured onto these molds placed in the bottom of a Petri dish. To speed the curing, these poured molds are baked. After the PDMS has cured, it is removed from on top of the mold and trimmed. In a chip with one set of channels forming a "T", three holes are cut into the silicone rubber at the ends of the "T", for example using a hole cutter similar to that used for cutting holes in cork, and sometimes called cork borers. These holes form the sample, waste and collection wells in the completed device. In this example, the hole at the bottom end of the T is used to load the sample. The hole at one arm of the T is used for collecting the sorted sample while the opposite arm is treated as waste. Before use, the PDMS device is placed in a hot bath of HCl to make the surface hydrophilic. The device is then placed onto a No. 1 (150 $\mu$m thick) (25×25 mm) square microscope cover slip. The cover slip forms the floor (or the roof) for all three channels and wells. The chip has a detection region as described above.

Note that any of or all of these manufacturing and preparation steps can be done by hand, or they can be automated, as can the operation and use of the device.

The above assembly is placed on an inverted Zeiss microscope. A carrier holds the cover slip so that it can be manipulated by the microscope's x-y positioning mechanism. This carrier also has mounting surfaces which support three electrodes, which implement the electro-osmotic and/or electrophoretic manipulation of the cells or particles to be analyzed and sorted. The electrodes are lengths of platinum wire taped onto a small piece of glass cut from a microscope slide. The wire is bent into a hook shape, which allows it to reach into one of the wells from above. The cut glass acts as a support platform for each of the electrodes. They are attached to the custom carrier with double-sided tape. This allows flexible positioning of the electrodes. Platinum wire is preferred for its low rate of consumption (long life) in electrophoretic and electro-osmotic applications, although other metals such as gold wire may also be used.

Device Loading

To operate the device for sorting, one of the wells, e.g. the collection or waste well, is first filled with buffer. All three channels, starting with the channel connected to the filled well, wick in buffer via capillary action and gravity. Preferably, no other well is loaded until all the channels fill with buffer, to avoid the formation of air pockets. After the channels fill the remaining wells can be loaded with buffer, as needed, to fill or equilibrate the device. The input or sample well is typically loaded last so that the flow of liquid in the channels is initially directed towards it. Generally, equal volumes of buffer or sample are loaded into each well. This is done in order to prevent a net flow of liquid in any direction once all of the wells are loaded, including loading the sample well with sample. In this embodiment, it is preferred that the flow of material through the device (i.e. the flow of sample) be driven only by the electrodes, e.g. using electro-osmotic and/or electrophoretic forces. The electrodes may be in place during loading, or they can be placed into the wells after loading, to contact the buffer.

Electrodes

Two of the above electrodes are driven by high voltage operational amplifiers (op-amps) capable of supplying voltages of +−150 V. The third electrode is connected to the electrical ground (or zero volts)of the high voltage op-amp electronics. For sorting operation the driven electrodes are placed in the collection and waste wells. The ground electrode is placed in the sample well. The op-amps amplify, by a factor of 30, a control voltage generated by two digital to analog converters (DACs). The maximum voltage these DACs generate is +−5 V, which determines the amplification factor of 30. The 150 V limit is determined by the power supply to the amplifiers, which are rated for +−175 V. These DACs reside on a card (a Lab PC 1200 Card, available from National Instruments, Austin, Tex.) mounted in a personal computer. The card also contains multiple channels of analog to digital converters (ADC's) one of which is used for measuring the signal generated by photomultiplier tubes (PMTs). This card contains two DACs. A third DAC can be used to drive the third electrode with an additional high voltage op amp. This would provide a larger voltage gradient, if desired, and some additional operational flexibility.

Without being bound by any theory, it is believed that the electrodes drive the flow of sample through the device using electro-osmotic or electrophoretic forces, or both. To start the movement of cells or particles to be sorted, a voltage gradient is established in the channels. This is done by generating a voltage difference between electrodes.

In this example, the voltage of the two driven electrodes is raised or lowered with respect to the grounded electrode. The voltage polarity depends on the charge of the cells or particles to be sorted (if they are charged), on the ions in the buffer, and on the desired direction of flow. Because the electrode at the sample well in the examples is always at zero volts with respect to the other two electrodes, the voltage at the "T" intersection or branch point will be at a voltage above or below zero volts, whenever the voltage of the other two electrodes is raised or lowered. Typically, the voltage is set or optimized, usually empirically, to produce a flow from the sample well, toward a downstream junction or branch point where two or more channels meet. In this example, where two channels are used, one channel is typically a waste channel and terminates in a waste well; the other channel is a collection channel and terminates in a collection well.

To direct the particles or cells to a particular channel or arm of the "T" (e.g. collection or waste), the voltage at the electrode in one well (or multiple wells, in multi-channel embodiments) is made the same as the voltage at the junction or branch point, where the channels meet. The voltage of the electrode at one well of the two or more wells is raised or lowered, to produce a gradient between that well and the branch point. This causes the flow to move down the channel towards and into the well, in the direction produced by the gradient. Typically, the voltage of the electrode at the waste well is raised or lowered with respect to the voltage at the collecting well, to direct the flow into the waste channel and the waste well, until a particle or cell is identified for collection. The flow is diverted into the collection channel and collection well by adjusting the voltages at the electrodes to eliminate or reduce the gradient toward the waste well, and provide or increase the gradient toward the collection well. For example, in response to a signal indicating that a cell has been detected for sorting, by examination in a detection region upstream of the branch point, the voltage at the waste and collection points can be switched, to divert the flow from one channel and well to the other.

The voltage at the branch point (the intersection voltage) is determined by the voltage gradient desired (e.g. Volts/mm) times the distance from the sample well electrode to the branch point (gradient x distance), which in this example is placed where all of the channels of the "T" intersect. The gradient also determines the voltage at the waste or collection electrode(gradient x distance from sample well to collection well).

Conceptually, the channels and wells of the "T" can be treated as a network of three resistors. Each segment of the "T" behaves as a resistor whose resistance is determined by the conductivity of the buffer and the dimensions of the channel. A voltage difference is provided across two of the resistors, but not the third. If the electrodes in each of the three wells is equidistant from the branch point, then each channel will have the same resistance.

For example, assume that each section of the "T" has 100 K ohms of resistance. If 100 volts is applied across two of the resistors and the third resistor is left unconnected, the current at the junction of the two resistors would be 50 volts. If a voltage source of 50 volts is connected to the end of the third resistor, the voltage at the junction does not change. That is, a net of zero volts is established across the third resistor; there is no voltage gradient and a flow is not initiated or changed. If a different voltage is applied, a gradient can be established to initiate or direct the flow into one channel or another. For example, to change the direction of flow from one arm of the "T" to the other, the voltage values of the two driven electrodes are swapped. The junction voltage remains the same. If the electrode distances from the "T" intersection are not equal, then the voltages can be adjusted to accommodate the resulting differences in the effective channel resistance. The end result is still the same. The electrode in the well of the channel which is temporarily designated not to receive particles or cells is set at the voltage of the "T" intersection. The voltage at the other driven electrode is set to provide a gradient that directs cell or particle flow into that well. Thus, cells or particles can be sent down one channel or another, and ultimately into one well or another, by effectively opening one channel with a net or relative voltage gradient while keeping the other channel or channels closed by a net or relative voltage gradient of zero.

In a preferred embodiment for sorting according to the invention, a slight flow down the channel that is turned "off" is desired. This keeps the particles or cells moving away from the branch point (the "T" junction), particularly those which have already been directed to that channel. Thus, a small non-zero gradient is preferably established in the "off" or unselected channel. The selected channel is provided with a significantly higher gradient, to quickly and effectively divert the desired cells or particles into that channel.

The placement of the wells and their electrodes with respect to the branch point, and in particular their distance from the branch point, is an important factor in driving the flow of particles or cells as desired. As the wells and electrodes are brought closer to the branch point, it becomes more important to precisely place the electrodes, or precisely adjust the voltages.

Detection Optics

In this example, a Ziess Axiovert 35 inverted microscope is used for detection of cells or particles for sorting. The objective lens of this microscope faces up, and is directed at the detection region of the described microfluidic chip, through the coverslip which in this example is the floor of the device. This microscope contains all the components for epifluorescence microscopy. See, Inoue pp 67–70, 91–97 (52). In this embodiment a mercury arc lamp or argon ion laser is used as the light source. The mercury lamp provides a broad spectrum of light that can excite many different fluorophores. The argon ion laser has greater intensity, which improves the detection sensitivity but is generally restricted to fluorophores that excite at 488 or 514 nm. The mercury lamp is used, for example, to sort beads as described elsewhere herein. The laser is used for sorting sorting GFP *E. coli* bacterial cells as described elsewhere herein. The high power argon ion beam is expanded to fill the illumination port of the microscope, which matches the optical characteristics of the mercury arc lamp and provides a fairly uniform illumination of the entire image area in a manner similar to the mercury lamp. However, it is somewhat wasteful of the laser light. If a lower powered laser is used, the laser light is focused down to coincide with the detection region of the chip, to achieve the same or similar illumination intensity and uniformity with less power consumption.

The objective used in the example is an Olympus PlanApo 60×1.4 N.A. oil immersion lens. The optics are of the infinity corrected type. An oil immersion lens enables collecting a substantial percentage of the 180 degree hemisphere of emitted light from the sample. This enables some of the highest sensitivity possible in fluorescence detection. This microscope has 4 optical ports including the ocular view port. Each port, except the ocular, taps ~20% of the available light collected from the sample when switched into the optical path. Only the ocular port can view 100% of the light collected by the objective. In this embodiment, a color video camera is mounted on one port, another has a Zeiss adjustable slit whose total light output is measured with a photomultiplier tube (PMT). The fourth port is not used.

The microscope focuses the image of the sample onto the plane of the adjustable slit. An achromatic lens collimates the light from the slit image onto the active area of the PMT. Immediately in front of the PMT window an optical band pass filter is placed specific to the fluorescence to be detected. The PMT is a side on-type and does not have a highly uniform sensitivity across its active area. By relaying the image to the PMT with the achromat, this non-uniformity is averaged and its effect on the measured signal is greatly minimized. This also enables near ideal performance of the bandpass filter. A 20% beam splitter has been placed in the light path between the achromat and filter. An ocular with a reticle re-images this portion of the collimated light. This enables viewing the adjustable slit directly, to insure that the detection area that the PMT measures is in focus and aligned. The adjustable slit allows windowing a specific area of the channel for detection. Its width, height, and x,y position are adjustable, and conceptually define a detection region on the chip. In this embodiment, the microscope is typically set to view a 5 $\mu$m (micron) length of the channel directly below the "T" intersection.

The PMT is a current output device. The current is proportional to the amount of light incident on the photocathode. A transimpedance amplifier converts this photocurrent to a voltage that is digitized by the Lab PC 1200 card. This allows for interpreting the image to select cells or particles having an optical reporter for sorting, as they pass through the detection region, based for example on the amount of light or fluorescence measured as an indication of whether a cell or particle has a predetermined level of reporter and should be chosen for collection. Voltages at the electrodes of the chip can be adjusted or switched according to this determination, for example by signals initiated by or under the control of a personal computer acting in concert with the Lab PC 1200 card.

Absorbence Detection

In another embodiment for detecting cells or particles, absorbence detection is employed, which typically uses relatively longer wavelengths of light, e.g., ultraviolet (UV). Thus, for example, a UV light source can be employed. Additional objective lenses can be used to image a detection region, such that the lenses are preferably positioned from the top surface if the PDMS device is made reasonably thin. Measurement of the light transmitted, i.e., not absorbed by the particle or cell, using an adjustable slit, e.g., a Zeiss adjustable slit as described above, is similar to that used in fluorescence detection. A spectrophotometer may also be used. As particles or cells pass through the detection window they attenuate the light, permitting detection of particles or cells having a desired characteristic and particles or cells that lack it. This can improve the accuracy of the particle sorting, for example, when sorting based on an amount of a characteristic, rather than presence of the characteristic alone, or to confirm a signal.

It is noted that in some cases, detection by absorbence may be detrimental at certain wavelengths of light to some biological material, e.g., *E. coli* cells at shorter (UV) wavelengths. Therefore, biological material to be sorted in this manner should first be tested first under various wavelengths of light using routine methods in the art. Preferably, a longer wavelength can be selected which does not damage the biological material of interest, but is sufficiently absorbed for detection.

Optical Trapping

In another embodiment, an optical trap, or laser tweezers, may be used to sort or direct cells in a PDMS device of the invention. One exemplary method to accomplish this is to prepare an optical trap, methods for which are well known in the art, that is focused at the "T" intersection proximate to, and preferably downstream of, the detection region. Different pressure gradients are established in each branch. A larger gradient at one branch channel creates a dominant flow of particles or cells, which should be directed into the waste channel. A second, smaller gradient at another branch channel should be established to create a slower flow of fluid from the "T" intersection to another channel for collection. The optical trap remains in an "off" mode until a desired particle is detected at the detection region. After detection of a desired characteristic, the particle or cell is "trapped", and thereby directed or moved into the predetermined branch channel for collection. The particle or cell is released after it is committed to the collection channel by turning off the trap laser. The movement of the cell or particle is further controlled by the flow into the collection well. The optical trap retains its focus on the "T" intersection until the detection region detects the next cell or particle.

Flow control by optical trapping permits similar flexibility in buffer selection as a pressure driven system. In addition, the pressure gradients can be easily established by adjusting the volume of liquid added to the wells. However, it is noted that the flow rate will not be as fast when the pressure in one channel is above ambient pressure and pressure in another is below.

Forward Sorting

In an electrode-driven embodiment, prior to loading the wells with sample and buffer and placing the electrodes, the electrode voltages are set to zero. Once the sample is loaded and the electrodes placed, voltages for the driven electrodes are set, for example using computer control with software that prompts for the desired voltages, for example the voltage differential between the sample and waste electrodes. If the three wells are equidistant from the "T" intersection, one voltage will be slightly more than half the other. In a typical run, the voltages are set by the program to start with directing the particles or cells to the waste channel. The user is prompted for the threshold voltage of the PMT signal, to identify a cell for sorting, i.e. diversion to the collection channel and well. A delay time is also set. If the PMT voltage exceeds the set threshold, the driven electrode voltages are swapped and then, after the specified delay time, the voltages are swapped back. The delay allows the selected particle or cell enough time to travel down the collection channel so that it will not be redirected or lost when the voltages are switched back. As described above, a slight gradient is maintained in the waste channel, when the voltages are switched, to provide continuity in the flow. This is not strong enough to keep the particle or cell moving into the other or "off" channel it if is too close to or is still at the branch point.

The value of this delay depends primarily on the velocity of the particles or cells, which is usually linearly dependent on the voltage gradients. It is believed that momentum effects do not influence the delay time or the sorting process. The particles or cells change direction almost instantaneously with changes in the direction of the voltage gradients. Unexpectedly, experiments have so far failed to vary the voltages faster than the particles or cells can respond. Similarly, experiments have so far shown that the dimensions of the channels do not effect the delay, on the distance and time scales described, and using the described electronics. In addition the speed with which the cells change direction even at high voltage gradients is significantly less than needed to move them down the appropriate channel, when using a forward sorting algorithm.

Once the voltage and delay value are entered the program, it enters a sorting loop, in which the ADC of the Lab PC 1200 card is polled until the threshold value is exceeded. During that time, the flow of particles or cells is directed into one of the channels, typically a waste channel. Once the threshold is detected, the above voltage switching sequence is initiated. This directs a selected cell or particle (usually and most preferably one at a time) into the other channel, typically a collection channel. It will be appreciated that the cells or particles are being sorted and separated according to the threshold criteria, without regard for which channel or well is considered "waste" or "collection". Thus, cells can be removed from a sample for further use, or they can be discarded as impurities in the sample.

After the switching cycle is complete (i.e. after the delay), the program returns to the ADC polling loop. A counter has also been implemented in the switching sequence which keeps track of the number of times the switching sequence is executed during one run of the program. This should represent the number of cells or particles detected and sorted. However, there is a statistical chance that two cells or particles can pass through simultaneously and be counted as one. In this embodiment, the program continues in this polling loop indefinitely until the user exits the loop, e.g. by typing a key on the computer keyboard. This sets the DACs (and the electrodes) to zero volts, and the sorting process stops.

Reverse Sorting

The reverse sorting program is similar to the forward sorting program, and provides additional flexibility and an error correction resource. In the event of a significant delay in changing the direction of flow in response to a signal to divert a selected cell or particle, for example due to momentum effects, reversible sorting can change the overall direction of flow to recover and redirect a cell or particle that is initially diverted into the wrong channel. Experiments using the described electrode array show a delay problem and an error rate that are low enough (i.e. virtually non-existent), so that reversible sorting does not appear necessary. The algorithm and method may be beneficial, however, for other embodiments such as those using pressure driven flow, which though benefitting from an avoidance of high voltages, may be more susceptible to momentum effects.

If a cell is detected for separation from the flow, and switching is not fast enough, the cell will end up going down the waste channel with all of the other undistinguished cells. However, if the flow is stopped as soon as possible after detection, the cell will not go too far. A lower driving force can then be used to slowly drive the particle in the reverse direction back into the detection window. Once detected for a second time, the flow can be changed again, this time directing the cell to the collection channel. Having captured the desired cell, the higher speed flow can be resumed until the next cell is detected for sorting. This is achieved by altering the voltages at the electrodes, or altering the analogous pressure gradient, according to the principles described above.

To move cells at higher velocities, for faster and more efficient sorting, higher voltages may be needed, which could be damaging to cells, and can be fatal to living cells. Preliminary experiments indicate that there may be a limit to the trade-off of voltage and speed in an electrode driven system. Consequently, a pressure driven flow may be advantageous for certain embodiments and applications of the invention. Reversible sorting may be advantageous or preferred in a pressure driven system, as hydraulic flow switching may not be done as rapidly as voltage switching. However, if a main or waste flow can move fast enough, there may be a net gain in speed or efficiency over voltage switching even though the flow is temporarily reversed and slowed to provide accurate sorting. Pressure driven applications may also offer wider flexibility in the use of buffers or carriers for sample flow, for example because a response to electrodes is not needed.

It will be appreciated by persons of ordinary skill in the art that the examples and preferred embodiments herein are illustrative, and that the invention may be practiced in a variety of embodiments which share the same inventive concept.

BIBLIOGRAPHY

1. J. P. Nolan, L. A. Sklar, *Nature Biotechnology* 16, 633 (1998).
2. P. J. Crosland-Taylor, *Nature (London)* 171, 37 (1953).
3. U.S. Pat. No. 2,656,508 issued to Coulter (1949).
4. L. A. Kamensky, M. R. Melamed, H. Derman, *Science* 150, 630 (1965).
5. A. Moldavan, *Science* 80, 188 (1934).
6. M. A. Van Villa, T. T. Trujillo, P. F. Mullaney, *Science* 163, 1213 (1969).
7. M. A. Van Villa, et al., A *fluorescent cellphotometer: a new method for the rapid measurement of biological cells stained with fluorescent dyes.* (Biological and Medical Research Group of the Health Division, LASL., 1997).
8. M. J. Fulwyer, *Science* 156, 910 (1974).
9. H. M. Shapiro, *Practical Flow Cytometry* (Wiley-Liss Inc., New York City, 1995).
10. M. R. Melamed, T. Lindmo, M. L. Mendelsohn, *Flow Cytometry and Sorting* (Wiley-Liss Inc., New York City, 1990).
11. G. Whitesides, Y. Xia, *Angewandte Chemie International Edition* 37, 550 (1998).
12. P. H. Li, D. J. Harrison, *Analytical Chemistry* 69, 1564 (1997).
13. S. Fiedler, et al. *Analytical Chemistry* 70, 1909–1915 (1998).
14. L. A. Sklar, *Proc. SPIE* 3256, 144 (1998).
15. H. P. Chou, A. Scherer, C. Spence, S. R. Quake, Proc. Natl. Acad. Sci. USA 96: 11–13 (1998).
16. A. Ashkin, J. M. Dziedzic, *Science* 235, 1517 (1987).
17. A. Ashkin, J. M. Dziedzic, *Nature* 330, 769 (1987).
18. T. N. Buican, M. J. Smyth, H. A. Verissman, *Applied Optics* 26, 5311 (1987).
19. C. Spence, S. R. Quake, "Transformation of cells with DNA sorting on microchips."; personal communication, 1998.
20. R. V. Hare, "Polyvinylsiloxane impression material."; U.S. Pat. No. 5,661,222, 1997.
21. M. U. Kopp et al., *Science*, 280: 1046 (1998)
22. D. J. Harrison et al., *Science*, 261: 895 (1993)
23. J. P. Brody, "Valveless Microswitch, U.S. Pat. No. 5,656,155 (1998).
24. Aine, H. E., et al., U.S. Pat. No. 4,585,209 (1986).
25. Baker, D. R., in Capillary Electrophoresis, John Wiley Sons, New York, 1995.
26. Ballantyne, J. P., eL al., J. Vac. Sci. Technol. 10:1094 (1973).
27. Castro, A., et al., Anal. Chem. 85:849–852 (1993).
28. Goodwin, P. M., et: al., Nucleic Acids Research 21(4) :803–806 (1993).
29. Gravesen, P., et: al., U.S. Pat. No. 5,452,878 (1995).
30. Haugland, R. P., in Handbook of Fluorescent Probes and Research Chemicals, 5th Ed., Molecular Probes, Inc., Eugene, Oreg. (1992).

31. Keller, R. A., et al., GB Patent No. 2,264,296 (October 1995).
32. Krutenat, R. C., Kirk-Othmer Concise Encyclopedia of Chemical Technology, John Wiley & Sons, New York (1985).
33. O'Connor, J. M., U.S. Pat. No. 4,581,624 (1986).
34. van Lintel, H. T. G., U.S. Pat. No. 5,271,274 (1993).
35. Wise, K. D., et al., U.S. Pat. No. 5,417,235 (1995).
36. Thompson, L. F., "Introduction to Lithography", ACS Symposium Series 219:1–13, (1983).
37. Angell et al., Scientific American 248:44–55 (1983).
38. Manz et al., Trends in Analytical Chemistry 10: 144–149 (1991)
39. Harrison et al., International Publication No. 98/52691, published Nov. 26, 1998.
40. Bein, Thomas, Efficient Assays for Combinatorial Methods for the Discovery of Catalysts, *Angew. Chem. Int. Ed.* 38:3, 323–26 (1999).
41. F. H. Arnold, *Acct. Chem. Research* 31, 125–131 (1998).
42. Hanes, J. & Pluckthun A. *Proc. Natl. Acad. Sci., USA* 94, 4937 (1997).
43. Hoffmuller, U. & J. Schneider-Mergener, *Angew. Chemie. Int. Ed.* 37, 3241–3243 (1998).
44. Jermutus, L., L. A. Ryabova & A. Pluckthun, *Curr. Opin. Biotechnol.* 9, 534–548 (1998).
45. Roberts, R. W. & Szostak, J. W. *Proc. Natl. Acad. Sci USA* 94, 12297–12302 (1997).
46. Stemmer, W. P. C. *Nature*, 370, 389 (1994).
47. Tawfik, D. and Griffiths, A. *Natl. Biotechnol.* 16, 656 (1998).
48. Sambrook et al., *Molecular Cloning: A Laboratory Manual* 2$^{nd}$ Edition, Cold Spring Harbor Laboratory Press (1989).
49. Benecke et al., U.S. Pat. No. 5,454,472 (1995).
50. J. Affholter and F. Arnold, "Engineering a Revolution," *Chemistry in Britain*, April 1999, p.48.
51. H. Joo, Z. Lin and F. Arnold, "Laboratory evolution of peroxide-mediated cytochrome P450 hydroxylation," *Nature* (1999), in press.
52. Inoue, Shinya and Spring, Kenneth R., Video Microscopy: The Fundamentals, 2nd ed., Plenum Press, New York, N.Y. (1997).

What is claimed is:

1. A method for sorting a fluid mixture of cells, which method comprises:

(a) providing the mixture of cells to a main channel of a microfabricated substrate, wherein the main channel is in fluid communication with at least two downstream branch channels which meet at a junction;

(b) producing a flow of fluid in the channel;

(c) interrogating each cell for a predetermined characteristic as it passes a detection region associated with the main channel; and (d) directing the flow of each cell into a selected branch channel according to the results of the interrogation, wherein the width and height of each channel is at least about two times as large as the diameter of the largest cell in the mixture of cells.

2. A method according to claim 1 in which the microfabricated substrate comprises a silicone elastomer.

3. A method according to claim 2 wherein the silicone elastomer comprises PolyDiMethylSiloxane (PDMS).

* * * * *